United States Patent [19]
Deghenghi

[11] Patent Number: 5,955,421
[45] Date of Patent: Sep. 21, 1999

[54] PEPTIDES CONTAINING D-2-ALKYL-TRYPTOPHAN

[76] Inventor: Romano Deghenghi, Chesaux-Dessus, St. Cergue, Switzerland, CH-1264

[21] Appl. No.: 08/971,032

[22] Filed: Nov. 14, 1997

Related U.S. Application Data

[60] Division of application No. 08/871,418, Jun. 9, 1997, which is a continuation-in-part of application No. 08/793,992, Mar. 6, 1997, abandoned, which is a continuation-in-part of application No. 08/530,853, Sep. 20, 1995, Pat. No. 5,795,957, which is a continuation-in-part of application No. 08/016,862, Feb. 10, 1993, Pat. No. 5,668,254, which is a continuation-in-part of application No. 07/672,300, Mar. 20, 1991, abandoned

[60] Provisional application No. 60/019,565, Jun. 11, 1996.

[30] Foreign Application Priority Data

| May 11, 1990 | [IT] | Italy | 20273-A |
| Sep. 27, 1994 | [IT] | Italy | MI94A1954 |
| Jun. 16, 1995 | [IT] | Italy | MI95A1293 |

[51] Int. Cl.$^6$ .......................... A61K 38/00; C07D 209/16
[52] U.S. Cl. .............................................. 514/2; 548/496
[58] Field of Search ................................... 514/2; 530/330

[56] References Cited

U.S. PATENT DOCUMENTS

| 3,316,260 | 4/1967 | Shen et al. | 530/330 |
| 3,816,254 | 6/1974 | Chibata et al. | 435/280 |
| 3,907,638 | 9/1975 | Uzuki et al. | 435/280 |
| 4,256,641 | 3/1981 | Batcho et al. | 548/497 |
| 4,481,362 | 11/1984 | Nakai et al. | 435/280 |
| 4,497,957 | 2/1985 | Nakai et al. | 548/496 |
| 5,057,615 | 10/1991 | Kono et al. | 548/497 |
| 5,212,069 | 5/1993 | Kula et al. | 435/228 |

FOREIGN PATENT DOCUMENTS

| 2 016 355 | 5/1990 | Canada . |
| 0 083 864 | 7/1983 | European Pat. Off. . |
| 0 203 031 | 11/1986 | European Pat. Off. . |
| 0 401 507 | 4/1990 | European Pat. Off. . |
| WO 88/09780 | 12/1988 | WIPO . |
| WO 89/07110 | 8/1989 | WIPO . |
| WO 91/18016 | 11/1991 | WIPO . |
| WO 94/07519 | 4/1994 | WIPO . |
| WO 95/14666 | 6/1995 | WIPO . |
| WO 96/15148 | 5/1996 | WIPO . |

OTHER PUBLICATIONS

Horwell et al. Eur. J. Med. Chem., 25, 53–60, Feb. 1990.
G. Tolis et al., "Growth Hormone Resease in Thalassemic Patients by a New GH–Releasing Peptide Administered Intravenously or Orally", 75th Endocrine Society meeting, Las Vegas, NE, Jun. 9, 1993.
R. Deghenghi et al., "Structure–Activity Studies with Hexarelin and Related GH–Releasing Peptides", 3rd Intl. Pituitary Congress, Marina de Rey, CA, Jun. 13–15, 1993.
E. Arvat et al., "GH–Releasing Activity of Hexarelin, A New Wynthetic Hexapeptide, After Intravenous, Subcutaneous, Intranasal and Oral Administration In Man", Giornate Endocrinologiche Pisane, Pisa (Italy) Jun. 28–29, 1993.
L.K. Conley et al., "Biological Potency of Hexarelin (EP23905), Initial Studies on Oral Activity", presented 1992.
W.B. Wehrenberg et al., "Biological Potency of Hexarelin (EP23905), A New Growth Hormone–Releasing Peptide", presented 1992.
R. Deghenghi et al., "Hexarelin (EP23905)—A Superactive Growth Hormone Releasing Peptide", presented in Milan, Italy, Sep. 1992.
L.K. Conley et al., "Studies on the Mechanism of Action of Hexarelin and GHRP–6", presented at International Symposium on Growth Hormone II, Basic Clinical Aspects, in Tarpon Springs, FL, Dec. 2–3, 1992.
B.P. Imbimbo et al., "Growth Hormone Releasing Activity of Hexarelin in Humans: A Dose–Responsive Study", presented at the International Symposium on Growth Hormone II, Basic Clinical Aspects, in Tarpon Springs, FL, Dec. 3–6, 1992.
Silver et al., "Scleroderma, Fascitis, and Eosinophilia Associated With The Ingestion of Tryptophan", *The New England Journal of Medicine*, 322:No. 13, (Mar. 29, 1990).
Karten et al., "Gonadotropin–Releasing Hormone Analog Design, Structure Function Studies Toward the Development of Agonists and Antagonists: Rationale and Perspective", *Endocrine Reviews*, 7(1):44–66 (1986).
Yabe et al., "Synthesis and Biological Activity of LH–RH Analogs Substituted by Alkyltryptophans at Position 3", *Chem. Pharm. Bull.*, vol. 27, No. 8 (1979).
Pailthorpe et al., *Chemical Abstracts* 79:400 (1973).
S. Majima, "E.W. Biologisches Verfahten der d–Tryptophandarstellans", *Hoppe–Seyler's Z. Physiol Chem.* 243:250 (1936).
Life Sciences, vol. 54, No. 18, 1994 pp. 1321–1328, R. Deghengi et al. "GH–Releasing Activity Of Hexarelin, a new growth hormone releasing peptide, in infant and adult rats".

*Primary Examiner*—Cecilia J. Tsang
*Assistant Examiner*—Michael Borin
*Attorney, Agent, or Firm*—Pennie & Edmonds LLP

[57] ABSTRACT

Peptides containing in its amino acid chain a D-2-alkylTryptophan residue wherein the alkyl group has between one and three carbon atoms and having pharmacological activity equal to or greater than that of analogous peptides containing natural unsubstituted D-Tryptophan residues in place of the D-2-alkylTryptophan. These peptides are more resistant to oxidative degradation which usually takes place, for example, in the presence of reactive radicals or during high energy sterilization than unsubstituted Tryptophan containing peptides.

10 Claims, 24 Drawing Sheets

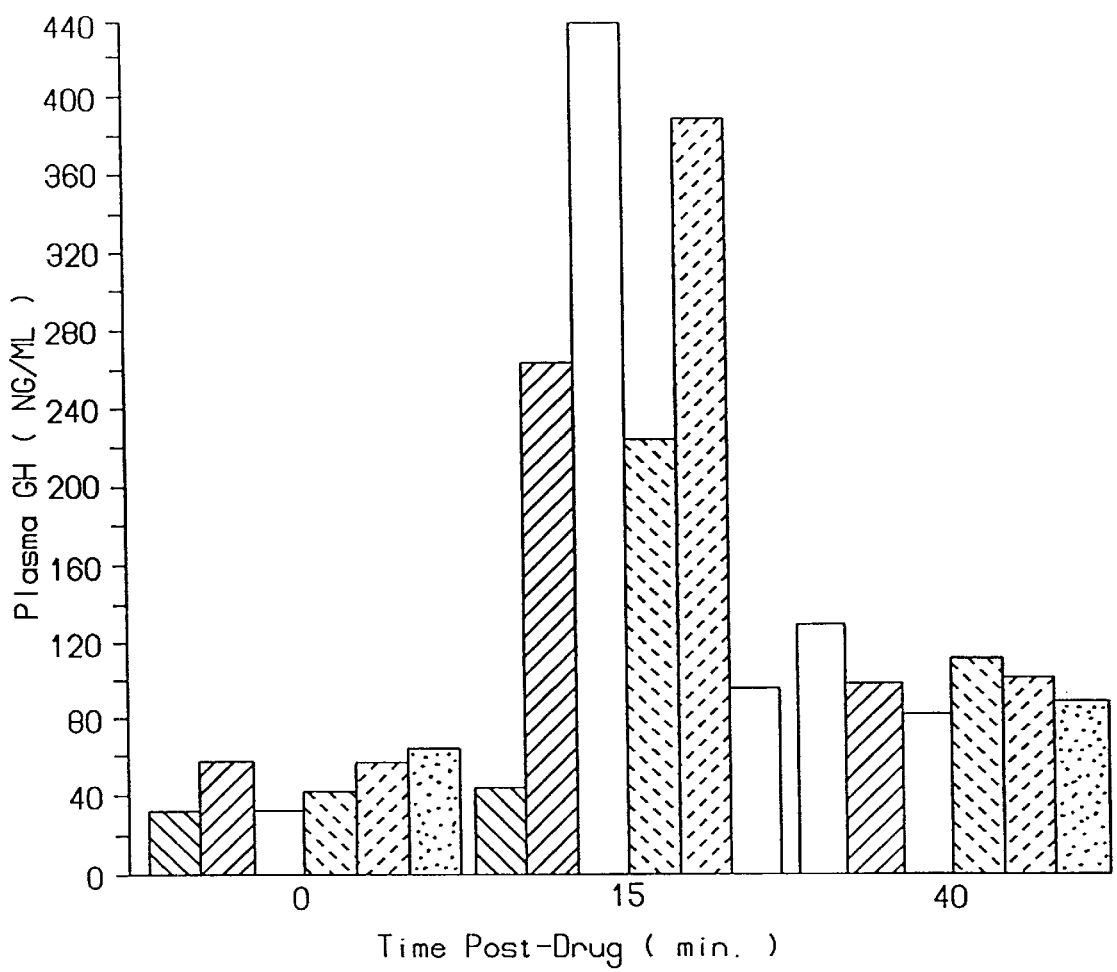
FIG. 11
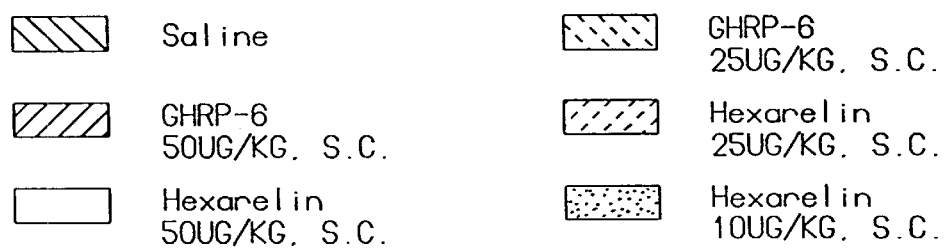

PEPTIDES CONTAINING D-2-ALKYL-TRYPTOPHAN

CROSS REFERENCE TO RELATED APPLICATIONS

The present application is a division of application Ser. No. 08/871,418, filed Jun. 9, 1997, which is a continuation-in-part of application Ser. No. 08/793,922 filed Mar. 6, 1997 now abandoned, a continuation-in-part of provisional application Ser. No. 60/019,565 filed Jun. 11, 1996, which is a continuation-in-part of application Ser. No. 08/530,853 filed Sep. 20, 1995, now U.S. Pat. No. 5,795,957, which is a continuation-in-part of application Ser. No. 08/016,862 filed Feb. 10, 1993, now U.S. Pat. No. 5,668,254, which is a continuation-in-part of application Ser. No. 07/672,300 filed Mar. 20, 1991, abandoned.

TECHNICAL FIELD

The present invention relates to the field of biologically active peptides. Specifically, this invention relates to biologically active peptides containing the amino acid D-Tryptophan ("D-Trp").

BACKGROUND ART

It is well known that the incorporation or substitution of a D-Tryptophan residue into a biologically active peptide chain enhances the activity of that chain. Furthermore, such incorporation or substitution will prolong the biological activity. The prolonged and enhanced effectiveness of such peptides probably relates the increased resistance to degradation by peptidases.

Examples of D-Tryptophan containing peptides are the LHRH agonists as described by D. H. Coy et al., *Journal of Medical Chemistry*, volume 19, page 423 (1976), W. Koenig et al., *Peptide Chemistry* (1987), T. Shiba and S. Sakakibara (eds.), Osaka, Protein Research Foundation, Osaka (1988), page 591, B. J. A. Furr et al., *Journal of Endocrinol. Invest.*, volume 11, page 535 (1988). Examples of D-Tryptophan containing somastostatin analogs, such as the peptides octreotide and vapreotide are disclosed by R. Deghenghi, *Biomedicine and Pharmacotherapy*, volume 42, page 585 (1988). Another example of a D-Tryptophan containing peptide are the synthetic antagonists of Substance P as disclosed by D. Regoli et al., *European Journal of Pharmacology*, volume 99, page 193, (1984), and GHRP-6 described by C. Y. Bowers et al., *Endocrinology*, volume 114, page 1537, (1984).

Peptides containing Tryptophan have been subject to degradation due to the "Kynurenine pathway". In this pathway, the enzyme Tryptophan pyrrolase (i.e., indolamine 2,3-dioxygenase) degrades the pyrrole ring of Tryptophan. Kynurenine and other breakdown products are generated by this degradation. Some of the breakdown products have been shown to be toxic when present in elevated concentrations as reported by R. M. Silver et al., *The New England Journal of Medicine*, volume 322, page 874, (1990).

D-Tryptophan containing peptides are subject to degradation by oxygen and other reactive radicals as reported by R. Geiger and W. Koenig, "The Peptides," Academic Press, volume 3, page 82, New York (1981). The D-Tryptophan in the peptide chain may react with active or activated groups when peptides are formulated in certain controlled delivery pharmaceutical compositions, such as those based on polylactic/polyglycolic acid polymers. Such degradation is thought to be facilitated by either heat or by the presence of catalysts. It is also possible that radiolysis products formed during ionizing sterilization of these pharmaceutical compositions may facilitate the breakdown of D-Tryptophan. Clearly, the breakdown of D-Tryptophan, and the concomitant breakdown of the pharmaceutical compound containing D-Tryptophan is an undesirable effect.

Yabe et al., *Synthesis and Biological Activity of LHRH Analogs Substituted by Alkyl Tryptophans at Position 3*, Chem. Pharm. Bul. 27 (8) pp. 1907–1911 (1979) discloses seven analogs of LHRH in which the Tryptophan residue at position 3 was replaced by various L-methyl Tryptophans and L-ethyl Tryptophans. However, each analog tested exhibited reduced hormonal activity compared to synthetic LHRH.

What is needed is a derivative of D-Tryptophan which retains the prolonged and increased biological activity discussed above, while resisting degradation by indolamine dioxygenase, oxygen or other reactive radicals. It is of course essential that such a derivative of D-Tryptophan would maintain biological activity as compared to D-Tryptophan containing bioactive peptides.

One use of such active peptides is for releasing growth hormone ("GH"). If sufficiently high GH levels are achieved in mammals after the administration of compounds capable of inducing such release, growth can be accelerated, muscular mass can be increased and production of milk can be enhanced. It is known that the increase of growth hormone levels in mammals can be achieved by administering growth hormone release agents, such as, for example, growth hormone release hormones (GHRH).

The increase of growth hormone levels in mammals can also be obtained by administering growth hormone release peptides. See, for example, the following U.S. Pat. Nos. 4,223,019, 4,223,020, 4,223,021, 4,224,316, 4,226,857, 4,228,155, 4,228,156, 4,228,157, 4,228,158, 4,410,512, 4,410,513, 4,411,890 and 4,839,344. Many of the peptides described in these patents have complex structures, are difficult to synthesize, purify and/or formulate into convenient dosage forms. Additionally, some of these have in vitro activity, but do not exhibit in vivo activity. Further, some of these peptides are not active when administered orally.

One of the more studied growth hormone release peptides is GHRP-6 (C. Y. Bowers et al., Endocrinology 114:1537 (1984) and has the formula His-D-Trp-Ala-Trp-D-Phe-Lys-NH$_2$. GHRP-6 releases growth hormone both in vitro and in vivo and is orally active in animals, including humans. Its molecular mechanism has been studied, as well as the molecular mechanism of its analogue heptapeptide GHRP-1 (Cheng et al., Endocrinology 124:2791 (1989); M. S. Akman et al., Endocrinology 132:1286 (1993)). It was found that contrary to natural GHRH, GHRP-1 and GHRP-6 act through different receptors for the release of GH and also via a different mechanism, which is independent from cAMP and which operates through other intracellular pathways, such as through the mobilization of calcium supplies and via a proteinkinase C (PKC)-dependent process (L. Bresson-Bépoldin and L. Dufy-Barbe, Cell. Calcium 15, 247 (1994)).

In view of the important effects that growth hormone releasing peptides can have on veterinary and human medicine, there remains a need for growth hormone releasing peptides that are more efficacious than those currently in existence, and as such, can be administered at a lower concentration and at a lower cost with fewer adverse health affects.

Therefore, rather simple, short chain oligopeptides capable of promoting growth hormone release that can be easily and conveniently prepared and that can be easily purified and formulated into a dosage form that can be administered via the oral route are presently desired. In particular, those oligopeptides exhibiting in vivo activity when administered orally are sought.

The terms "biological effect" or "pharmacological effect" as used in the present disclosure refer to the qualitative effect that a bioactive peptide has upon living tissue. As an example, LHRH, luteinizing hormone releasing hormone, has the biological effect of causing cells of the anterior pituitary gland to release luteinizing hormone. In contrast, the term "potency" is used in its conventional sense to refer to the degree and duration of the bioactivity of a given peptide.

Utilizing these terms as defined above, what is needed is a Tryptbphan containing bioactive peptide which is resistant to oxidative degradation and reactive radical attack while maintaining the same biological activity and a similar or greater potency than the presently available analogous peptides provide.

SUMMARY OF INVENTION

The present invention relates to certain defined peptides that contain a D-2-alkylTryptophan ("D-2-Mrp") residue to enhance or increase the biological activity of the peptide. The alkyl group is substituted at the number 2 position of the Tryptophan, and typically includes 1 to 3 carbons, such as methyl, ethyl, propyl or isopropyl, and is preferably a methyl group.

When known, biologically active peptides that contain Tryptophan are modified to replace the tryptophan with a D-2-alkyl Tryptophan, improved resistance to oxidative breakdown is achieved while maintaining or enhancing the biological activity of the peptide.

These peptides generally have a sequence of two to ten amino acids, wherein at least one amino acid is the D-2-alkylTryptophan. In some peptides, at least two amino acids are D-2-alkylTryptophan, in adjacent positions in the sequence.

One embodiment of the invention relates to peptides which enhance the release of growth hormone in vivo. These peptides have one of the following formulae:

  A—D—X—Z—B      (I)

  E—D—Mrp—(Ala)$_n$—F—G      (II)

  J—D—X—Mrp—NH$_2$      (III)

wherein

A is hydrogen, 2-aminoisobutyryl, or 4-aminobutyryl;

D stands for the dextro isomer,

X is a 2-alkyltryptophan of formula (IV):

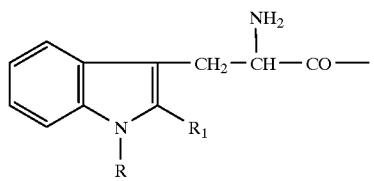

wherein R is hydrogen, CHO, SO$_2$CH$_3$, mesitylene-2-sulfonyl, PO$_3$(CH$_3$)$_2$, PO$_3$H$_2$, wherein R$_1$ is a C$_1$–C$_3$ alkyl group (e.g., methyl, ethyl, propyl or isopropyl), or X is a residue of protected serine, Ser (Y), wherein Y can be benzyl, p-chlorobenzyl, 4-methoxybenzyl, 2,4,6-trimethoxybenzyl, or t-butyl, B is NR$_2$R$_3$, wherein R$_2$ and R$_3$, which can be the same or different, are hydrogen, a C$_1$–C$_3$ alkyl group, an OR$_4$ group, wherein R$_4$ is hydrogen, a C$_1$–C$_3$ alkyl, or a C-Lys-NH$_2$ group, wherein C is Phe, Mrp or D-Mrp;

Z is D-Mrp, D-βNal or Mrp;

E is any natural L-amino acid or its D-isomer, imidazolylacetyl, isonipecotinyl, 4-aminobutyryl, 4-(aminomethyl) cyclohexanecarbonyl, Glu-Tyr-Ala-His, Tyr-Ala-His, Tyr-His, D-Thr-His, D-Ala, D-Thr, Tyr and Gly;

n is 0 or 1;

F is selected from the group consisting of Trp, D-Trp, Phe and D-β-Nal;

G is selected from the group consisting of NH$_2$, D-Phe-Lys-NH$_2$, Phe-Lys-NH$_2$, D-Trp-Lys-NH$_2$, D-Phe-Lys-Thr-NH$_2$, D-Phe-Lys-D-Thr-NH$_2$ and an O-C$_1$–C$_3$ alkyl group, with the proviso that E is not His when F is L-Trp or D-Trp and when G is D-Phe-Lys-NH$_2$; and J is hydrogen, 4-aminobutyryl (or GAB) or D-Mrp.

Additional peptides are disclosed which are useful for enhancing the activity of hormones acting on the hypothalamic pituitary axis. These peptides have the following formula:

  K—D—2—Mrp—M   (V)

wherein

K is Ala-His-, D-Phe-Cys-Phe-, D-Phe-Cys-Tyr-, Arg-D-Trp-N-methyl-Phe-, D-pyro-Gln-Gln-D-Trp-Phe-, or pyro-Glu-His-Trp-Ser-Tyr-; and M is Met-NH$_2$, Leu-Met-NH$_2$, Leu-Arg-Pro-NH$_2$, Leu-Arg-Pro-Gly-NH$_2$, Ala-Trp-D-Phe-Lys-NH$_2$, Lys-Val-Cys-Trp-NH$_2$, or Lys-Thr-Cys-NHCH(CH$_2$OH)CHOHCH$_3$.

Preferred peptides have the following formula:

  P—D—Mrp—(D—Q)$_n$—T      (VI)

wherein

P is hydrogen, 2-aminoisobutyryl, 4-aminobutyryl, imidazolylacetyl, isonipecotinyl, or 4-(aminomethyl)-cyclohexanecarbonyl (or tranexamyl);

D stands for the dextro isomer;

Mrp is a 2-alkyltryptophan of formula (IV);

Q is Trp, Mrp, or β-Nal;

n is 0, 1 or 2; and

T is OCH$_2$CH$_5$, NH$_2$, Mrp-NH$_2$, Mrp-Lys-NH$_2$, Lys-NH$_2$, or Phe-Lys-NH$_2$;

with the proviso that, when P is 4-aminobutyryl or 4-(aminomethyl)-cyclohexanecarbonyl, Q is not β-Nal; and when P is H or 4-aminobutyryl, n is not 1 when T is NH$_2$.

Any pharmaceutically acceptable salt of these peptides can also be used. Addition salts with pharmaceutically acceptable organic or inorganic acids are preferred.

Another embodiment of the invention relates to a method for enhancing the biological activity and oxidation resistance of a peptide by formulating a composition comprising one of the peptides described above and administering a therapeutically effective amount of the composition to an animal. Advantageously, the animal is a human, and the peptide is administered in an amount of about 0.1 μg to about 10 μg of total peptide per kg of body weight.

The pharmaceutical composition which contain a therapeutically effective amount of one of these peptides, optionally in admixture with a carrier or an excipient, form another embodiment of the invention. These compositions can be provided in the form of a composition for parenteral, intranasal, oral, or controlled release administration, or as a subcutaneous implant, where the peptide is administered orally in an amount of about 30 µg to about 1000 µg of peptide per kg of body weight. The peptide is typically in the form of a pharmaceutically acceptable addition salt, and the carrier can be a biodegradable polymer matrix so that the composition is in a controlled release dosage form. Implants are conveniently used for this purpose.

BRIEF DESCRIPTION OF THE DRAWINGS

FIGS. 6–11 are graphical representations of GH release in anesthetized male rats following subcutaneous administration of saline, GHRP-6 and HEXARELIN;

DETAILED DESCRIPTION OF THE INVENTION

Figure 1:
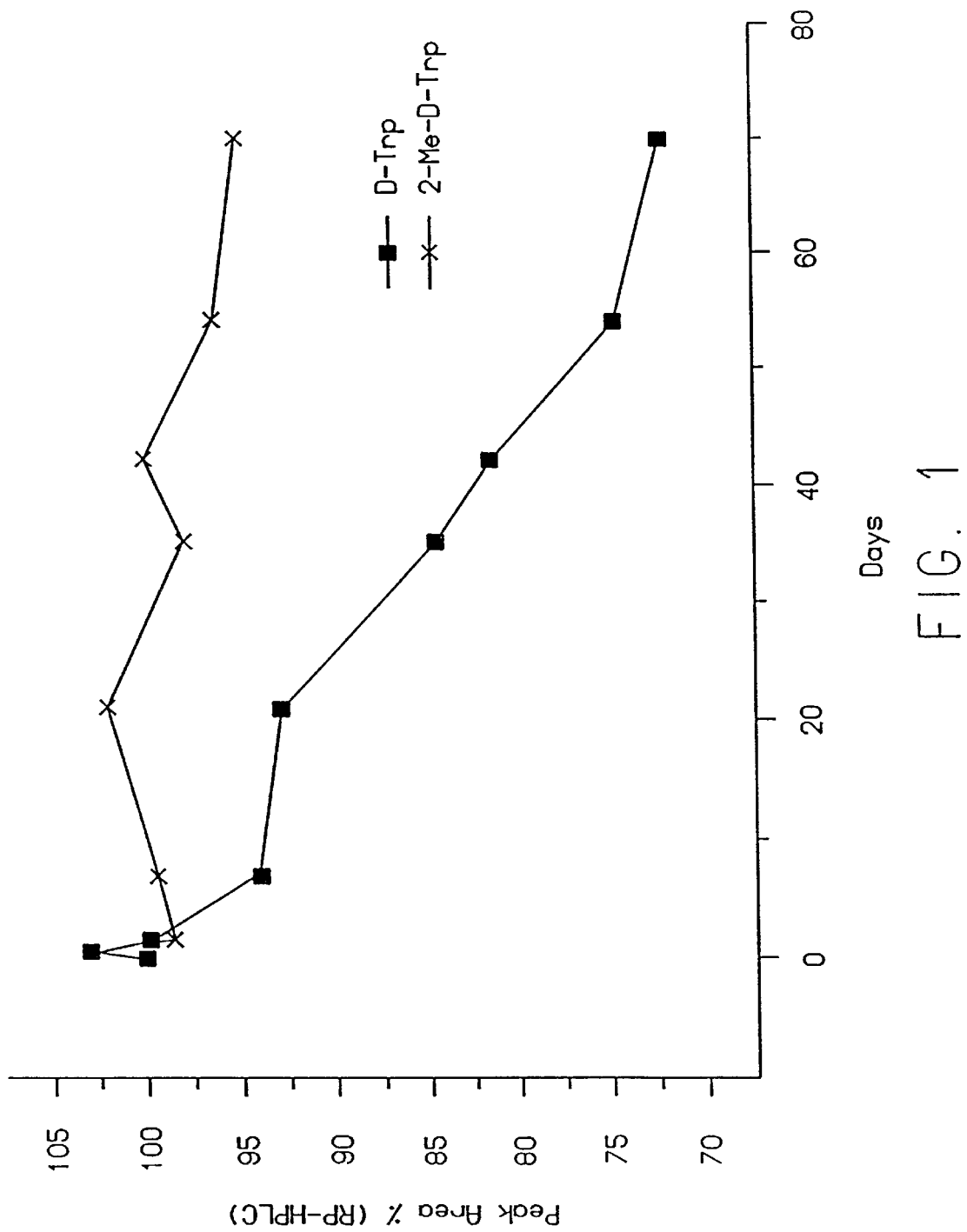
FIG. 1 is a graphical representation of the stability of D-Trp and D-2-methyl-Trp in an acid solution.

Now in accordance with the present invention, a derivative of D-Tryptophan has been discovered which enhances or increases the biological activity of certain peptides, or which imparts to biologically active peptides incorporating that derivative improved resistance to the oxidative breakdown reaction of Tryptophan, while maintaining or increasing the biological activity and pharmacological effect compared to peptides incorporating unaltered D-Tryptophan.

Specifically, the present invention relates to a Tryptophan derivative, namely D-2-Mrp, in which the alkyl substituent in the 2 position is a lower alkyl group, preferably one containing 1 to 3 carbon atoms. Peptides incorporating D-2-Mrp are more stable in the presence of reactive radicals or when pharmaceuticals containing such peptides are exposed to ionizing radiation.

This invention also describes a more practical synthesis of D-2-Mrp and the preparation of novel protected D-2-Mrp derivatives particularly suited for use in the synthesis of peptides.

A particularly preferred biologically active peptide containing this modified Tryptophan derivative is an analog of GHRP (Growth Hormone Releasing Peptide), His-D-2-alkyl-Trp-Ala-Trp-D-Phe-Lys-NH$_2$, which is referred to in the trade as HEXARELIN. Additional biologically active peptides include:

Ala-His-D-2-alkyl-Trp-Ala-Trp-D-Phe-Lys-NH$_2$,
Pyro-Glu-His-Trp-Ser-Tyr-D-2-alkyl-Trp-Leu-Arg-Pro-Gly-NH$_2$,
Pyro-Glu-His-Trp-Ser-Tyr-D-2-alkyl-Trp-Leu-Arg-Pro-NHCH$_2$CH$_3$,
D-Pro-Gln-Gln-D-Trp-Phe-D-Trp-2-alkyl-Trp-Met-NH$_2$,
Arg-D-Trp-N-methyl-Phe-D-2-alkyl-Trp-Leu-Met-NH$_2$,
D-Phe-Cys-Phe-D-2-alkyl-Trp-Lys-Thr-Cys-NHCH(CH$_2$OH) CHOHCH$_3$ and
D-Phe-Cys-Tyr-D-2-alkyl-Trp-Lys-Val-Cys-Trp-NH$_2$ where alkyl designates a lower alkyl group, preferably comprising 1 to 3 carbons. The methyl group is most preferred due to simplicity of manufacture.

The first peptide mentioned above, named HEXARELIN, is an analog of GHRp and is used for stimulating the release of growth hormone. The second peptide is an analog of the first and contains one additional amino acid.

The third and fourth peptides listed above are analogs of the natural peptide Pyro-Glu-His-Trp-Ser-Tyr-Trp-Leu-Arg-Pro-Gly-NH$_2$, which is a luteinizing hormone releasing hormone (LH-RH), i.e., a neurohumoral hormone produced in the hypothalamus which stimulates the secretion of the LH luteinizing hormone by the anterior pituitary gland. These peptides pertain therefore to the class of LHRH agonists and are also defined respectively as follows:

[D-2-methyl-Trp$^6$]LHRH and [Des-Gly$^{10}$-D-2-methyl-Trp$^6$-Pro-ethylamide$^9$]LHRH.

The fifth and sixth peptides listed above are antagonists of substance P. Substance P is a neurotransmitter used by sensory neurons that convey responses of pain or other noxious stimuli to the central nervous system. Accordingly, these peptides have analgesic and anti-inflammatory effects.

The seventh and eighth peptides are analogs (agonists) of somatostatin and as such show antisecretory and antitumoral activity.

Although the aforementioned examples of the present invention disclose specific embodiments thereof, it is believed that the substitution of an D-2-Mrp in bioactive peptide containing at least one Tryptophan residue will yield bioactive peptides providing the advantages and benefits discussed above.

The incorporation of a D-2-Mrp in bioactive peptides as described above provides a method for prolonging and preserving the activity of such peptides. When analogous bioactive peptides not substituted with a D-2-Mrp are exposed to various processing conditions and substances, the activity of such peptides may be adversely effected. Sterilizing procedures used in the pharmaceutical industry may expose bioactive compounds to ionizing radiation. Such radiation may effect the formation of reactive radicals. Tryptophan containing peptides are particularly susceptible to attack by such radicals and such attack may render the peptide ineffective, or possibly toxic. Furthermore, various formulating compounds, such as polylactic-polyglycolic acid polymers may contain active, or activated groups which may also attack Tryptophan containing bioactive peptides. The present invention provides a method for protecting a tryptophan containing bioactive peptide from these manufacturing hazards while also increasing the peptides resistance to oxidative degradation after formulation is complete.

It is believed that the presence of the alkyl group at the number 2 position of the Tryptophan increases the stability of the pyrrole ring wherein attack by reactive radicals and active or activated groups occurs.

2-methyl-Tryptophan is known (cf. H. N. Rydon, J. Chem. Soc. 1948, 705) and the homologous alkylated derivatives are conveniently prepared from the corresponding 2-alkyl indoles by well known methods (cf. J. P. Li et al., *Synthesis* (1), 73, 1988). The resolution of the racemic Tryptophan derivatives to give the D-enantiomers of the present invention can be achieved by a variety of methods (cf. Amino Acids, Peptides and Proteins, Vol. 16, pages 18–20, The Royal Society of Chemistry, London, 1985). Specifically, S. Majima (Hoppe-Seyler's Z. Physiol. Chem. 243, 250 (1936) describes the digestion of 2-methyl tryptophan with colibacteria with isolation of the undigested D-isomer.

A more practical synthesis of D-2-methy tryptophan is presented in Example 1. In general, D-2-Mrp can be prepared by a method which comprises treating a solution of racemic N$^\alpha$-acetyl-2-alkyl-Tryptophan with acylase for a sufficient time and at a sufficient temperature to form insoluble material therein, recovering and lyophilizing the insoluble fraction to form a residue, dissolving the residue in a suitable solvent, subjecting the solvent and dissolved residue to chromatography to obtain highly polar fractions and lesser polar fractions, collecting the lesser polar fractions to obtain a N$^\alpha$-acetyl-D-2-alkyl-Tryptophan compound and hydrolyzing this compound to obtain D-2-Mrp.

In this method, the racemic N$\alpha$-acetyl-2-alkyl-Tryptophan is treated by dissolution in water with a base, such as potassium hydroxide, and retaining the solution for about 24 hours at about 40° C. The N$\alpha$-acetyl-D-2-alkyl-Tryptophan is then hydrolyzed under an inert gas, such as nitrogen, with a base, such as KOH or NaOH, for about 24 hours at 100° F., prior to the addition of an acid, such as acetic acid, and the cooling of the solution. Also, the insoluble fraction can be obtained by filtration and the residue may be formed by lyophilizing the insoluble fraction to dryness. It is preferred for the residue to be dissolved in the upper phase of N-BaOH-AcOH-H$_2$O before being introduced into the chromatography column.

Both the solution phase or the solid phase method of peptide synthesis can be used to make the peptides of this invention, (cf. R. Geiger et al., "The Peptides", Academic Press, New York 1981). If the solid phase method is used, peptide synthesizers such as the Applied Biosystem 430A, Bioresearch Sam 9500 or the Beckman Model 990 are preferably used. According to this methodology, the first amino acid is linked to the benzhydrylamine resin and the remaining protected amino acids are then coupled in a step wise manner using the standard procedures recommended by the manufacturers of the synthesizers. For instance, amino acid couplings are performed by using symmetrical anhydrides in the Applied Biosystems Synthesizer and diisopropylcarbodiimide in the Bioresearch or Beckman machines. The amino acid derivatives are protected by the tertiary butoxy-carbonyl groups or by Fmoc (9-Fluorenyl methoxycarbonyl) groups on the alpha-amino function during the synthesis. The functional groups present in the amino-acid in the side chain are previously protected, e.g. by acetyl(Ac), benzoyl (Bz), t-butyloxycarbonyl (Boc), benzyloxymethyl (Bom), benzyl (Bzl), benzyloxycarbonyl (Z), formyl (For), p-nitro-phenyl ester (ONp), tosyl (Tos), etc. For instance, the functional groups of Histidine are protected by benzyloxymethyl (His(Bom)), tosyl (His(Tos)), the functional groups of Tryptophan by formyl (Trp(For)), those of Serine by benzyl (Ser(Bzl)), those of Tyrosine by 2-Br-benzyloxycarbonyl (Tyr(2-Br-Z)), those of Arginine by tosyl (Arg(Tos)), those of Leucine by O-benzyl-p-tosyl (Leu(O-Bzl-p-Tos)), those of Proline by O-benzyl HCl (Pro(O-Bzl HCl)), those of Glycine by O-benzyl HCl (Gly (O-Bzl HCl)), those of Cysteine by 4-methyl-benzyl (Cys(4-Me-Bzl)), those of Lysine by benzyloxycarbonyl (Lys(Z)), those of Threonine by benzyl-OH (Thr(Bzl-OH)), those of Valine by O-benzyl-tosyl (Val(O-Bzl-p-Tos)), those of Glutamic Acid by O-benzyl (Glu(O-Bzl)), those of Methionine by P-nitrophenyl ester (Me(Onp)), and those of Alanine by O-benzyl HCl (Ala(O-Bzl HCl).

The Boc protective groups on the alpha-aminic function are removed at each stage by treatment with 60% trifluoroacetic acid ("TFA") in dichloromethane. Cleavage of Trp and Met containing peptides from the resin with simultaneous removal of all side-chain protecting groups is achieved as described by J. P. Tam et al.,*J. Am. Chem. Soc.*, Vol 105, page 6442 (1983). The crude peptides after HF cleavage are purified on a Sephadex G-50 F column in 50% acetic acid or by preparative reverse phase HPLC using gradients of acetonitrile and water containing 0.1% trifluoroacetic acid.

Another embodiment of the present invention relates to a number of short-chain oligopeptides which promote the release and increase of growth hormone levels in blood of animals by including in the peptide chain a D-Mrp residue. In a completely surprising manner it has now been found that very short oligopeptides, having at least one D-2-Mrp residue, have activity releasing growth hormone (GH) from somatotropes. Another unexpected distinctive feature of the present invention is the very high potency and the favorable oral activity/oral potency ratio that even the smallest tripeptides of the series exhibit.

It has also been found that the introduction of a D-2-Mrp residue in oligopeptides of the GHRP series, modifies the intracellular mechanism of GH release. In addition, the introduction of D-2-Mrp into a GHRP results in a substantial increase of the activity of the adenylcyclase in the anterior pituitary glands, both of murine origin, and of human origin.

Another unexpected characteristic feature of the present invention is the very high potency of penta-, hexa-, and heptapeptides and the favorable oral activity/potency ratio of shorter-chained tri- and tetrapeptides of the series.

Short chain oligopeptides within the scope of the present invention are defined by the following formulae:

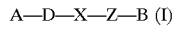

wherein

A is hydrogen, 2-aminoisobutyryl (i.e., alpha-aminoisobutyric acid), or 4-aminobutyryl (i.e. gamma-aminoisobutyric acid);

D relates to the dextro isomer,

X is Mrp, i.e., a 2-alkyltryptophan of formula (IV):

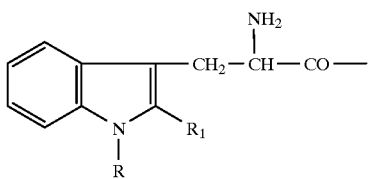

wherein
R is hydrogen, CHO, SO$_2$CH$_3$, mesitylene-2-sulfonyl, PO$_3$(CH$_3$)$_2$, PO$_3$H$_2$, wherein R$_1$ is a C$_1$–C$_3$ alkyl group (e.g., methyl, ethyl, propyl or isopropyl), or X is a residue of protected serine, Ser (Y), wherein Y can be benzyl, p-chlorobenzyl, 4-methoxybenzyl, 2,4,6-trimethoxybenzyl, or t-butyl, B is NR$_2$R$_3$, wherein R$_2$ and R$_3$, which can be the same or different, are hydrogen, a C$_1$–C$_3$ alkyl group, an OR$_4$ group, wherein R$_4$ is hydrogen, a C$_1$–C$_3$ alkyl, or a C-Lys-NH$_2$ group, wherein C is Phe, Mrp or D-Mrp;

Z is D-Mrp, D-βNal or Mrp;

E is any natural L-amino acid or its D-isomer, imidazolylacetyl, isonipecotinyl, 4-aminobutyryl, 4-(aminomethyl)cyclohexanecarbonyl, Glu-Tyr-Ala-His, Tyr-Ala-His, Tyr-His, D-Thr-His, D-Ala, D-Thr, Tyr and Gly;

n is 0 or 1;

F is selected from the group consisting of Trp, D-Trp, Phe and D-β-Nal;

G is selected from the group consisting of NH$_2$, D-Phe-Lys-NH$_2$, Phe-Lys-NH$_2$, D-Trp-Lys-NH$_2$, D-Phe-Lys-Thr-NH$_2$, D-Phe-Lys-D-Thr-NH$_2$ and an O—C$_1$–C$_3$ alkyl group, with the proviso that E is not His when F is L-Trp or D-Trp and when G is D-Phe-Lys-NH$_2$; and J is hydrogen, GAB or D-Mrp.

Also included are any addition salts of any pharmaceutically acceptable organic or inorganic acids of any one of these short chain oligopeptides.

The abbreviations for the residues of amino acids herein used are in agreement with the standard nomenclature for the peptides: e.g.,
Gly=Glycine
Tyr=L-Tyrosine
Ile=L-Isoleucine
Glu=L-Glutamic Acid
Thr=L-Threonine
Phe=L-Phenylalanine
Ala=L-Alanine
Lys=L-Lysine
Asp=L-Aspartic Acid
Cys=L-Cysteine
Arg=L-Arginine
Gln=L-Glutamine
Pro=L-Proline
Leu=L-Leucine
Met=L-Methionine
Ser=L-Serine
Asn=L-Asparagine
His=L-Histidine
Trp=L-Tryptophan
Val=L-Valine
D-β-Nal=D-9-Naphthylalanine
Moreover, the following abbreviations are also used:
Aib=2-aminoisobutyryl;
GAB=4-aminobutyryl;
INIP=Isonipecotinyl IMA=Imidazolylacetyl
Mrp=2-alkyltryptophan
Bzl=benzyl;
p-Cl-Bzl=p-chlorobenzyl;
Mob=4-methoxybenzyl;
Tmob=2,4,6-trimethoxybenzyl;
tbu=tert-butyl;
For=formyl;
Mts=mesitylene-2-sulfonyl.

According to the present invention, alkyl means lower alkyl, comprising from 1 to 3 carbon atoms. Examples of lower alkyl are methyl, ethyl, propyl, isopropyl. Among these, the methyl group is most preferred.

All the three letter-abbreviations of the amino acids preceded by a "D" indicate the D-configuration of the amino acid residue. When the amino acid is referred to with the only three-letter abbreviation, it has L configuration.

In addition, the peptides of the present invention can bear, on the C-terminus thereof, a C$_1$–C$_3$ alkyl ester, wherein alkyl is selected from the group consisting of methyl, ethyl, n-propyl and iso-propyl.

As used herein, "natural L-amino acid" refers to an amino acid bearing the L-configuration and being found in nature. Examples of natural L-amino acids include, but are not limited to L-tyrosine, L-isoleucine, L-glutamic acid, L-threonine, L-phenylalanine, L-alanine, L-lysine, L-aspartic acid, L-cysteine, L-arginine, L-glutamine, L-proline, L-leucine, L-methionine, L-serine, L-asparagine, L-histidine, L-tryptophan and L-valine.

As used herein, "therapeutically effective" means an amount or dose which, when administered to the animal including human, patient or subject, renders a benefit or an effect of increasing the level of cellular proteins such as hormones, or renders a benefit or an effect of treating or preventing an abnormal biological condition or disease.

As used herein, "EC$_{50}$" refers to the effective concentration for 50% of the peptides.

The most preferred growth hormone-release peptides of the present invention are:
GAB-D-Mrp-D-Mrp-Phe-Lys-NH$_2$;
GAB-D-Mrp-D-Mrp-Mrp-Lys-NH$_2$;
Aib-D-Mrp-D-Mrp-NH$_2$;
Aib-D-Mrp-Mrp-NH$_2$;
Aib-D-Ser(Bzl)-D-Mrp-NH2; and
GAB-D-Mrp-D-βNal-Phe-Lys-NH$_2$
INIP-D-Mrp-D-Trp-Phe-Lys-NH$_2$;
INIP-D-Mrp-D-β-Nal-Phe-Lys-NH$_2$;
IMA-D-Mrp-D-Trp-Phe-Lys-NH$_2$;
IMA-D-Mrp-D-β-Nal-Phe-Lys-NH$_2$;
GAB-D-Mrp-D-Trp-Phe-Lys-NH$_2$;
GAB-D-Mrp-D-β-Nal-Phe-Lys-NH$_2$;
GAB-D-Mrp-D-β-Nal-NH$_2$;
GAB-D-Mrp-D-β-Nal-OC$_2$H$_5$;
imidazolylacetyl-D-Mrp-Ala-Trp-D-Phe-Lys-NH$_2$;
imidazolylacetyl-D-Mrp-D-Trp-Phe-Lys-NH$_2$;
imidazolylacetyl-D-Mrp-D-β-Nal-Phe-Lys-NH$_2$;
4-(aminomethyl)cyclohexanecarbonyl-D-Mrp-D-Trp-Phe-Lys-NH$_2$;
4-(aminomethyl)cyclohexanecarbonyl-D-Mrp-D-β-Nal-Phe-Lys-NH$_2$;
D-Ala-D-Mrp-Ala-Trp-D-Phe-Lys-NH$_2$;
D-Thr-D-Mrp-Ala-Trp-D-Phe-Lys-NH$_2$;
His-D-Mrp-Ala-Phe-D-Trp-Lys-NH$_2$;
His-D-Mrp-Ala-Trp-D-Phe-Lys-Thr-NH$_2$;
His-D-Mrp-Ala-Trp-D-Phe-Lys-D-Thr-NH$_2$;
Tyr-His-D-Mrp-Ala-Trp-D-Phe-LysNH$_2$;
His-D-Mrp-Ala-TrpNH$_2$;

D-Thr-His-D-Mrp-Ala-Trp-D-Phe-Lys-NH$_2$; and
D-Thr-D-Mrp-Ala-TrpNH$_2$.

Pharmaceutically acceptable salts of the oligopeptide compounds of the present invention include but are not limited to organic or inorganic addition salts such as for example hydrochloride, hydrobromide, phosphate, sulfate, acetate, succinate, ascorbate, tartrate, gluconate, benzoate, malate and fumarate salts.

These peptides are preferably administered by the oral route, but they also can be administered intranasally, buccally or parenterally. These compounds (i.e., oligopeptides of the present invention) can be formulated into controlled release dosage forms, such as, biodegradable microcapsules, microspheres, subcutaneous implants and the like. Other controlled release dosage forms, though not specifically listed, are known to those skilled in the art and are within the scope of the present invention.

The peptides according to the present invention can be synthesized according to the usual methods of peptide chemistry, both solid-phase and solution, or by means of the classical methods known in the art. The solid-phase synthesis starts from the C-terminal end of peptide. A suitable starting material can be prepared, for example, by attaching the required protected alpha-amino acid to a chloromethylated resin, a hydroxymethylated resin, a benzylhydrylamine resin (BHA), or to a paramethylbenzylhydrylamine resin (p-Me-BHA). More particularly, for example, a chloromethylated resin is sold with the Trade Mark BIOBEADS (R) SX 1 by BioRad Laboratories, Richmond, Calif. The preparation of the hydroxymethyl resin is described by Bodansky et al., Chem. Ind. (London) 38, 15997, (1966). The BHA resin is described by Pietta and Marshall, Chem. Comm., 650 (1970) and is commercially available from Peninsula Laboratories Inc., Belmont, Calif.

After the starting attachment, the alpha-amino acid-protecting group can be removed by means of different acid reagents, comprising trifluoroacetic acid (TFA) or hydrochloric acid (HCl) dissolved in organic solvents at room temperature. After the removal of the alpha-amino acid-protecting group, the remaining protected amino acids can be coupled step by step in the desired order. Each protected amino acid can generally be reacted in excess of about three times using a suitable carboxyl activating group, such as dicyclohexylcarbodiimide (DCC) or diisopropylcarbodiimide (DIC) dissolved, for example, in methylene chloride (CH$_2$Cl$_2$) or dimethylformamide (DMF) and mixtures thereof. After the desired amino acid sequence has been completed, the desired peptide can be cleaved from the supporting resin by treatment with a reagent such as hydrogen fluoride (HF), which not only cleaves the peptide from the resin, but also the more common protecting groups of the lateral chains. When a chloromethylated resin or a hydroxymethylated resin is used, the treatment with HF leads to the formation of the acid peptide in free form. When a BHA or p-Me-BHA resin is used, the treatment with HF directly leads to the formation of the amide peptide in free form.

The above discussed sold-phase procedure is known in the art and was described by Atherton and Sheppard, Solid Phase Peptide Synthesis (IRL Press, Oxford, 1989).

Some methods in solution, which can be used to synthesize the peptide moieties of the present invention are detailed in Bodansky et al., Peptide Synthesis, 2nd edition, John Wiley & Sons, New York, N.Y. 1976 and from Jones, The Chemical Synthesis of Peptides, (Clarendon Press, Oxford, 1994).

These compounds can be administered to animals and humans at an effective dose which can be easily determined by one of ordinary skill in the art and which can vary according to the specie, age, sex and wight of the subject to be treated. For example, in humans, when intravenously administered, the preferred dose falls in the range from about 0.1 $\mu$g to about 10 $\mu$g of total peptide per kg of body weight. When orally administered, typically higher amounts are necessary. For example, in humans for the oral administration, the dosage level is typically from about 30 $\mu$g to about 1000 $\mu$g of peptide per kg of body weight. The exact level can be easily determined empirically by the skilled artisan.

Compositions useful for releasing growth hormone in an animal, including a human, can comprise a peptide of the present invention or a pharmaceutically acceptable salt thereof, or combinations of peptides of the present invention or pharmaceutically acceptable salts thereof, optionally, in admixture with a carrier excipient, vehicle, diluent, matrix or delayed release coating. Examples of such carriers, excipients, vehicles and diluents, can be found in *Remington's Pharmaceutical Sciences*, Eighteenth Edition, A. R. Gennaro, Ed., Mack Publishing Company, Easton, Pa., 1990. The delayed release pharmaceutical forms, comprising bioerodible matrixes suitable for subcutaneous implant are particularly useful. Examples of these matrices are described in WO 92/22600 and WO 95/12629.

The following examples are only provided as being illustrative of preferred embodiments of the present invention and are not intended to limit the breadth and scope of the invention as is readily understood by those skilled in the art.

EXAMPLES

The following examples illusrtate the method of making and activity of the peptides which represent preferred embodiments of the invention:

Example 1
Synthesis of D-2-Methyl-Tryptophan

N$^{\alpha\alpha}$-Acetyl-2-methyl-D,L-tryptphan [Y. Yabe et al. Chem. Pharm. Bull 27(8) 1907–1911 (1979)] 1.3 g (5 mmol), was suspended in 50 ml of water and dissolved by adding concentrated ammonium hydroxide to a pH of 7.5. 5 mg of acylase (from porcine kidney, Sigma Grade III lyophilized) was added and the mixture kept at 40° C. for 24 hours. The insoluble material was separated by filtration and the filtrate was lyophilized to dryness. The residue was dissolved in the upper phase (10 ml) of n-BuOH-AcOH-H$_2$O (16:1:20) and chromatographed on a 3.5×50 cm column of Sephadex G-25 (Pharmacia, Fluka) collecting 10 ml fractions. The less polar fractions (N° 16–25) were pooled to give mainly undigested N$^\alpha$-acetyl-2-methyl-D-tryptophan which, without purification, was hydrolyzed under N$_2$ with a solution of 1 g KOH in 25 ml of water at 100° F. for 24 hours. Acetic acid (2 ml) and water (10 ml) were added to the hot solution and placed in the refrigerator for 12 hours. The crude resulting 2-methyl-D-tryptophan was filtered, washed and dried and recrystallized from hot water (charcoal) to yield the title compound, m.p. 244–246°, [$\alpha$]$_D^{20}$+18.6, [c0.26(H$_2$O)].

Figure 2:
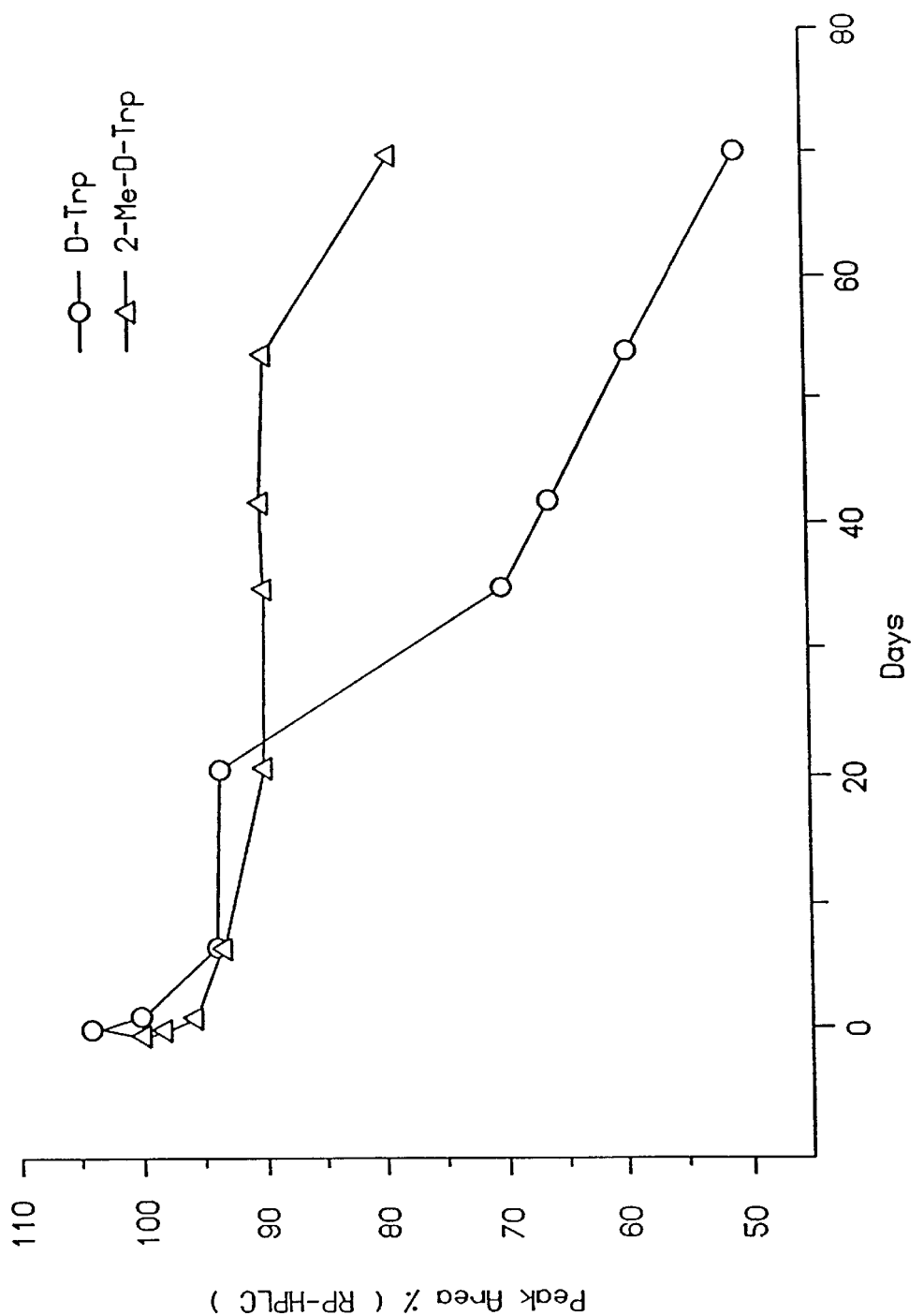
FIG. 2 is a graphical representation of the oxidative degradation of D-Trp and D-2-methyl-Trp in solution.

The enhanced stability of the 2-methyl-Tryptophan derivative is illustrated in FIGS. 1 and 2. In FIG. 1, the stability of this derivative is compared to D-Trp for 1% solutions at a pH of 2.2 (0.2 M citrate buffer with 0.02% NaN$_3$ added) which are maintained in the dark under helium, while FIG. 2 shows the oxidative degradation of these compounds in 1% solutions at a pH of 5.4 (0.2M acetate buffer with 0.02% NaN$_3$ added) under oxygen and constant light. The peak area is measured by HPLC.

The results show that the substituted Trp is stable for 60 days or longer, whereas the unsubstituted Trp began to lose stability after about 20 days.

Example 1a
Synthesis of Fmoc-D-2-Methyl-Trp
N$^\alpha$-[9 Fluorenylmethyloxycarbonyl]-2-methyl-D-Tryptophan (Fmoc derivative)

To a suspension of 436 mg of 2-methyl-D-Tryptophan of Example 1 (2 mMole) in 5 ml of water, a solution of 710 mg (2.1 mMole) of Fmoc-OSu (9 FluorenylmethyloxyN-hydroxysuccinimide) in 2 ml of dioxane is added dropwise and the mixture is stirred overnight at room temperature. The mixture is extracted with ether and the ether phase discarded. The aqueous phase is adjusted to pH 1 with 6N HCl and extracted with ethylacetate. The organic phase is washed with water, dried over $Na_2SO_4$ and evaporated in vacuo. The residue is dissolved in ether and hexane is added to precipitate the crystalline product which is filtered and dried.

M.p. 196–198° C. TLC: Rf 0.45 in $CHCl_3$/MeOH/AcOH85/10/5

|  | C | H | N |
| --- | --- | --- | --- |
| Calculated | 73.62% | 5.49% | 6.36% |
| Found: | 73.72% | 5.29% | 6.27% |

Additional suitably protected 2-Methyl-D-Tryptophans have the formula:

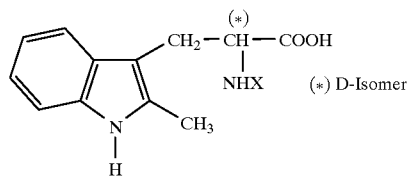

Where X is BZ (Benzoyl) or Z (Benzyloxycarbonyl). These can be prepared by conventional methods, starting from the 2-Methyl-D-Tryptophan.

Examples 2–9

Peptides which include the D-2-methyl Trp were made as follows:

Example 2
Pyro-Glu-His-Trp-Ser-Tyr-D-2-alkyl-Trp-Leu-Arg-Pro-Gly-$NH_2$,

The protective groups for the side chains are Tosyl (Tos) for Arginine and Histidine and Bromo-benzyloxycarbonyl (2-Br-Z) for Tyrosine. The benzhydrylamine resin (2.2 g) (Bachem®), was cross-linked at 1% with Proline and the apparatus used was a Beckman Model 990. The amino acids protected by Boc (tert-butyloxycarbonyl) are coupled with dicyclohexylcarbodiimide. The Boc groups are removed by trifluoroacetic acid in methylene chloride.

The synthesis yielded 4.07 g of the decapeptide-resin (98% of theoretical weight gain). Part of this resin (1.5 g) was stirred at 0° centigrade for 30 minutes with HF (24 ml) and anisole (8 ml). HF was then removed as rapidly as possible (ca. 60 min) in vacuo and EtOAc was added to the thus obtained residue. Solid material was filtered, washed with EtOAc, dried, and extracted with 2 M AcOH. Lyophilization gave a white powder which was purified by gel filtration on a column (2.5×95 cm) of Sephadex G-25 (fine) by elution with 2 M ACOH. The eluate portion corresponding to the major peak was then dried and eluted further on a column (2.5×95 cm) of Sephadex G-25 (fine) previously equilibrated with the lower phase followed by the upper phase of the following biphasic solvent mixture n-BuOH-AcOH-$H_2O$ (4:1:5). Elution with the upper phase gave a major peak and the peptide from this area was collected, concentrated to dryness, and lyophilized from dilute AcOH to give the titled peptide as a white powder. Amino acid analysis was consistent with the desired structure.

Example 3
Pyro-Glu-His-Trp-Ser-Tyr-D-2-alkyl-Trp-Leu-Arg-Pro-NHCH$_2$CH$_3$, The peptide was assembled on a 1% cross-linked Pro-Merrifield resin (2.0 g, 1.0 mmol of Pro) using the same conditions and protecting groups employed in Example 1, with the exception that dinitrophenol group protection was used for the imidazole group of histidine. The peptide-resin obtained (3.45 g) was stirred with ethylamine (20 ml, 0° C.) for 6 hours and excess amine was removed in vacuo. The protected peptide resin was extracted with MeOH and precipitated by the addition of a large excess of EtOAc to give 1.36 g of material. The obtained product was treated and deprotected with HF-anisole and crude peptide obtained after this treatment was purified by gel filtration followed by partition chromatography to yield the homogeneous peptide cited. Amino acid analysis was consistent with the desired structure.

Examples 4–9

Using the above described methods with appropriate modifications well known to the skilled in the art particularly the use of Fmoc derivatives as protected amino acids of Example 1a for the preparation of Fmoc-D-2 Methyl Trp or other suitably protected amino acids, the following peptides are synthesized:

Example 4
His-D-2-alkyl-Trp-Ala-Trp-D-Phe-Lys-NH$_2$ ("HEXARELIN"),

Example 5
Ala-His-D-2-alkyl-Trp-Ala-Trp-D-Phe-Lys-NH$_2$,

Example 6
D-Pro-Gln-Gln-D-Trp-Phe-D-Trp-2-alkyl-Trp-Met-NH$_2$,

Example 7
Arg-D-Trp-N-methyl-Phe-D-2-alkyl-Trp-Leu-Met-NH$_2$,

Example 8
D-Phe-Cys-Phe-D-2-alkyl-Trp-Lys-Thr-Cys-NHCH(CH$_2$OH) CHOHCH$_3$ and

Example 9
D-Phe-Cys-Tyr-D-2-alkyl-Trp-Lys-Val-Cys-Trp-NH$_2$.

The peptides of Examples 4 and 5 were tested as Growth Hormone releasers in rats. GH released in a series of seven 10-day old rats, injected subcutaneously with a standard dose of 160 μg/kg and sacrificed 15 minutes after the injection. Results are as follows:

| Samples | GH (ng/kg) |
| --- | --- |
| Untreated Controls | 14.64 + 21.41 |
| Example 4 | 201.00 + 39.55 |
| Example 5 | 212.00 + 48.63 |

Thus, the peptides of Examples 4 and 5 (i.e., His-D-2-methyl-Trp-Ala-Trp-D-Phe-Lys-$NH_2$ and Ala-His-D-2-methyl-Trp-Ala-Trp-D-Phe-Lys-$NH_2$) were found to be very active analogs.

Example 10

The peptide of Example 4 (i.e., HEXARELIN) was compared with GHRP-6 {Bowers C. Y., Momany F. A., Reynolds G. A., and Hong A. (1984) On the in Vitro and in Vivo Activity of a New Synthetic Hexapeptide that Acts on the Pituitary to Specifically Release Growth Hormone, Endocrinology, 114: 1537–1545} both in vitro and in vivo, as follows.

Male Sprague Dawley rats (Charles River, Calco, Italy) of 2–3 months of age were used. Rats were housed at 22 +2° C., with lighting cycle of 14 h light: 10 h dark (lights on from 06.00 to 20.00 h), at least 10 days before starting the experiments. A standard dry diet and water were available ad libitum.

In Vitro Experiments
Pituitary Cell Culture

Pituitary tissue used for cell dissociation included only the anterior lobe. Briefly, pituitary glands were collected in sterile F-10 medium and after cutting into small fragments incubated twice (30 minutes each) at 37° C. in F-10 medium containing 6% fetal calf serum and collagenase (2.5 mg/ml) (Boehringer, Mannheim GmbH, Germany). Fragments were then washed in Dulbecco's PBS, $Ca^{2+}$ and $Mg^{2+}$ free medium and mechanically dissociated. Single cell suspension was planted onto 24-well ($2\times10^5$ cells/well) culture plates. The cells were incubated in F-10 medium supplemented with 10% horse serum, 4% fetal calf serum and gentamycin (25 µg/ml), in a humidified atmosphere of 5% $CO_2$ and 95% air at 37° C.

After 3 days, the medium was removed and the cells washed twice with serum free F-10, then incubated with 1 ml of F-10 containing 0.1% BSA only, or with added various concentrations of synthetic peptides.

After incubation for 2 h at 37° C., media were collected and stored frozen at −20° C. until assayed for measurement of GH content.

In Vivo Experiments
Experimental Procedure

Between 09.00–10.00 h rats were anesthetized with ketamine (58 mg/kg, Inoketam, VIRBAC, Milano) and xilazine (12 mg/kg, Rompun, Bayer, Milano). Thirty minutes later, a blood sample (250 µg) was withdrawn from the exposed jugular vein, peptides were injected intravenously or subcutaneously, and further blood samples were collected 10, 20 and 30 minutes later.

Medium and plasma GH was measured by radioimmunoassay using materials supplied by the NIADDK Bethesda, Md. Values were expressed in term of NIASSK-rat-GH-RP-2 standard (potency 2 IU/ml), as ng/ml of medium or plasma.

The minimum detectable value of rat was 1.0 ng/ml; intra-assay variability was 6%. To avoid inter-assay variation, samples from each experiment were assayed simultaneously. The results were as follows:

In Vitro Experiments

When pituitary cell monolayers were incubated for two hours with increasing concentrations ($10^{-8}$ to $10^{-6}$ M) of HEXARELIN and GHRP-6, stimulation of GH secretion over basal secretion was observed. Comparison of the GH secretion levels obtained after stimulation of pituitary cell monolayers with GHRP-6 and HEXARELIN indicates that their activities were very similar, as shown in Table 1.

TABLE 1

GH-RELEASING ACTIVITY OF GHRP-6 AND HEXARELIN

| TREATMENT | CONCENTRATION (M) | | | |
| --- | --- | --- | --- | --- |
| | 0 | $10^{-8}$ | $10^{-7}$ | $10^{-6}$ |
| GHRP-6 | 484.2 ± 11.4 | 544.2 ± 23.9 | 526.5 ± 19.0 | 510.0 ± 12.0 |
| HEXARELIN | 471.1 ± 31.3 | 557.8 ± 15.9 | 589.1 ± 17.9 | 558.0 ± 19.1 |

Pool of controls 492.5±12.4 GH (ng/well)

Values (ng/well) are the means +S.E.M. of 6 determinations per group.

Pituitary cell monolayers were incubated with peptides for 2 hours.

In Vivo Experiments

In anesthetized rats the administration of graded doses (150, 300 and 600/µg/kg) of HEXARELIN elicited significant increases of plasma GH concentrations 10 and 20 minutes after administration. Similar results were obtained after injection of the same doses of GHRP-6, as shown in Table 2.

TABLE 2

COMPARISON OF THE GH-RELEASING ACTIVITY OF GHRP-6 (A) AND HEXARELIN (B) ADMINISTERED I.V. IN MALE RATS ANESTHETIZED WITH KETAMINE AND XILAZINE

| TREAT-MENT | TIME (minutes) | | | |
| --- | --- | --- | --- | --- |
| | 0 | 10 | 20 | 30 |
| Control | 19.8 ± 5.8(8) | 45.6 ± 7.5(8) | 28.7 ± 4.8 | 32.2 ± 4.5(4) |
| A 150 µg/kg | 30.2 ± 7.8(7) | 394.0 ± 31.0(7) | 139.3 ± 10.2(7) | 42.5 ± 4.5(4) |
| B 150 µg/kg | 15.0 ± 2.9(8) | 412.7 ± 39.7(8) | 132.2 ± 12.7(8) | 44.0 ± 6.0(4) |
| A 300 µg/kg | 21.9 ± 4.4(8) | 413.6 ± 21.5(8) | 162.7 ± 22.1(8) | 38.2 ± 7.7(4) |
| B 300 µg/kg | 13.5 ± 2.0(7) | 438.5 ± 26.8(7) | 213.8 ± 34.2(7) | 48.1 ± 8.8(3) |
| A 600 µg/kg | 21.2 ± 6.1(8) | 542.0 ± 38.0(8) | 195.5 ± 11.0(8) | 64/0 ± 11.9(4) |
| B 600 µg/kg | 18.4 ± 4.3(8) | 478.3 ± 19.8(8) | 164.2 ± 13.2(8) | 54.5 ± 13.3(4) |

Values (ng/ml) are means±S.E.M.

Number of rats are shown in parentheses and refer to pooled data of 2–3 experiments in which similar data were obtained.

Figure 3:
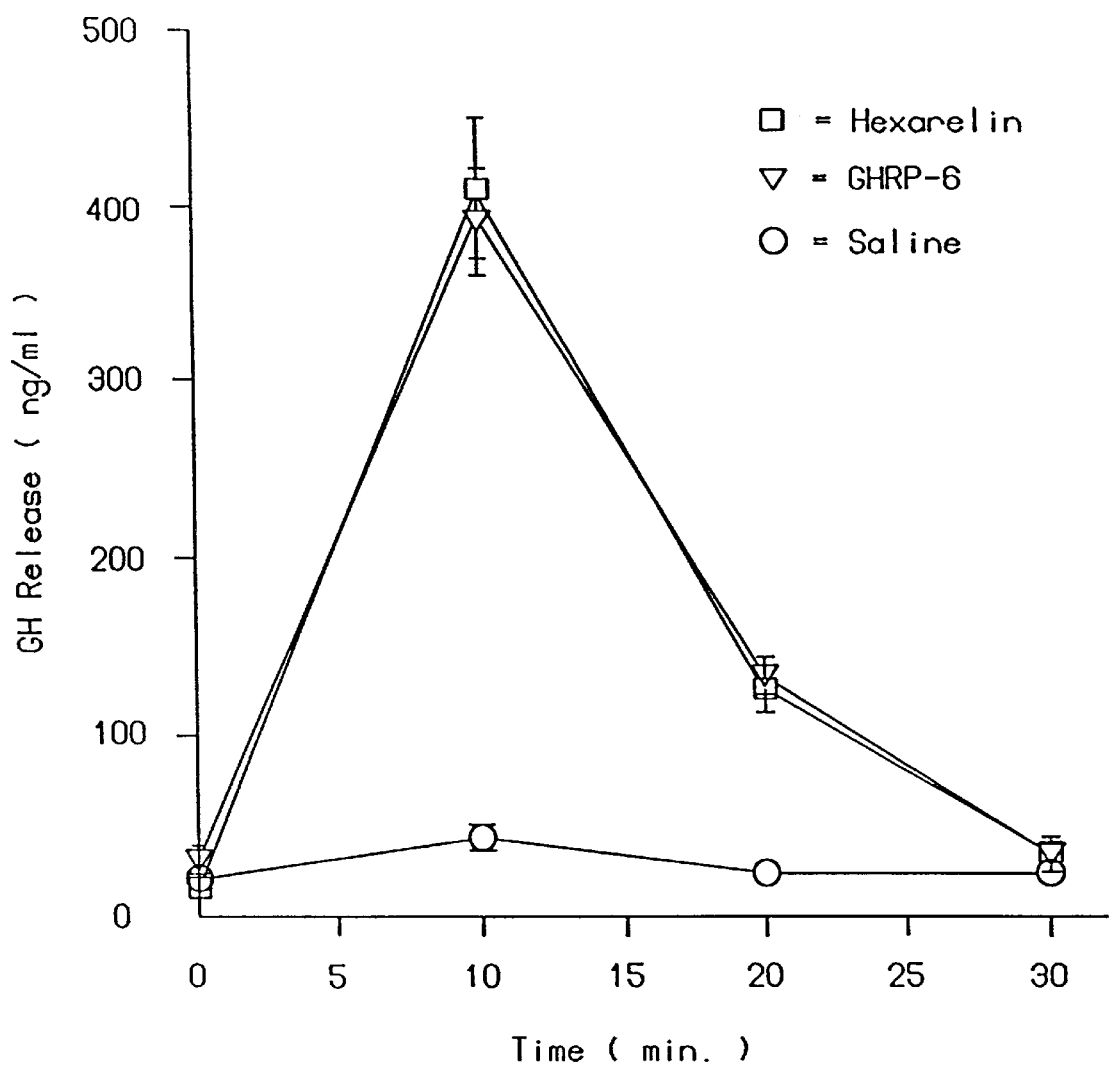
FIGS. 3–5 are graphical representations of GH release in anesthetized male rats following intravenous administration of saline, GHRP-6 and HEXARELIN.
Figure 4:
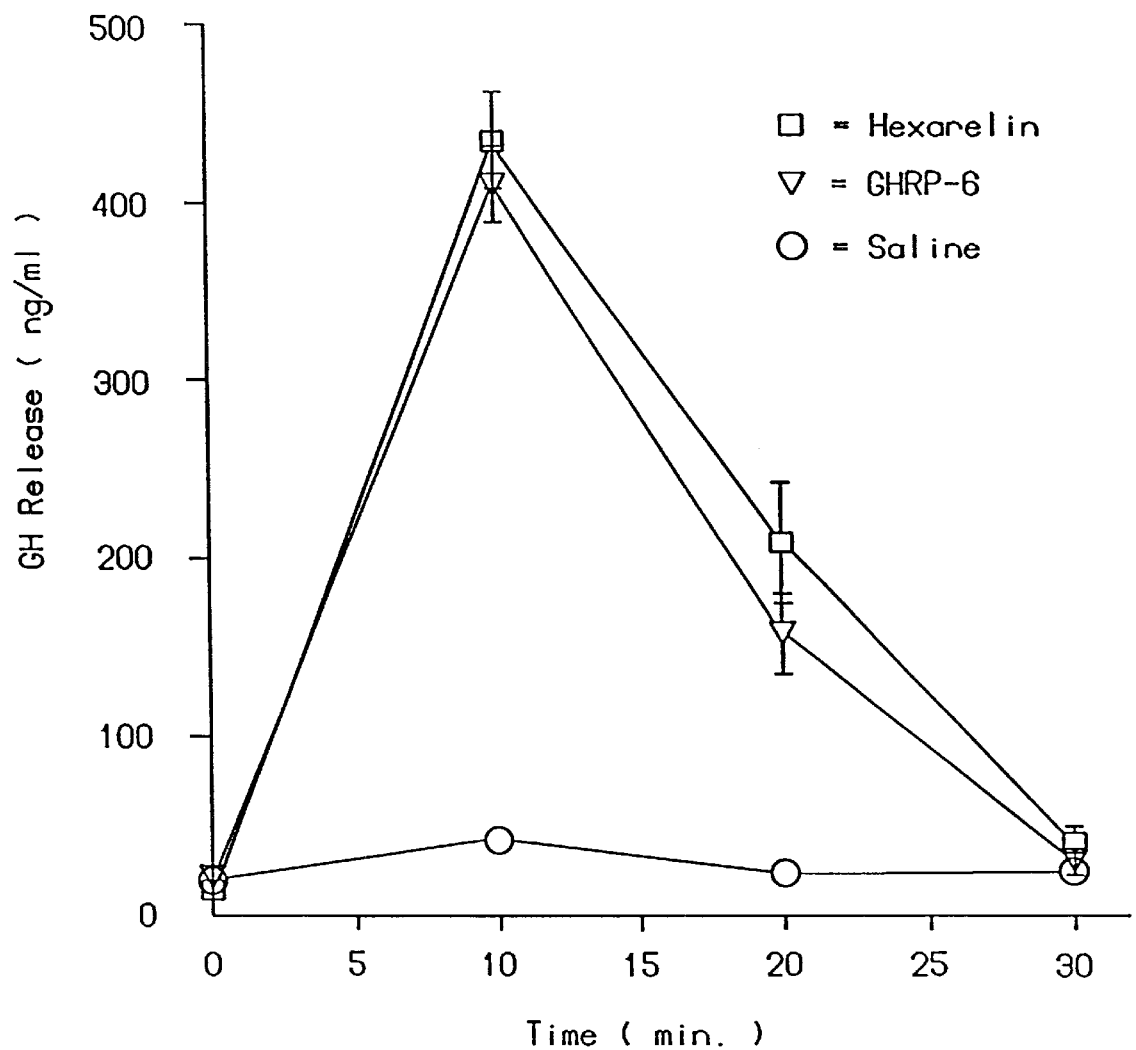
Figure 5:
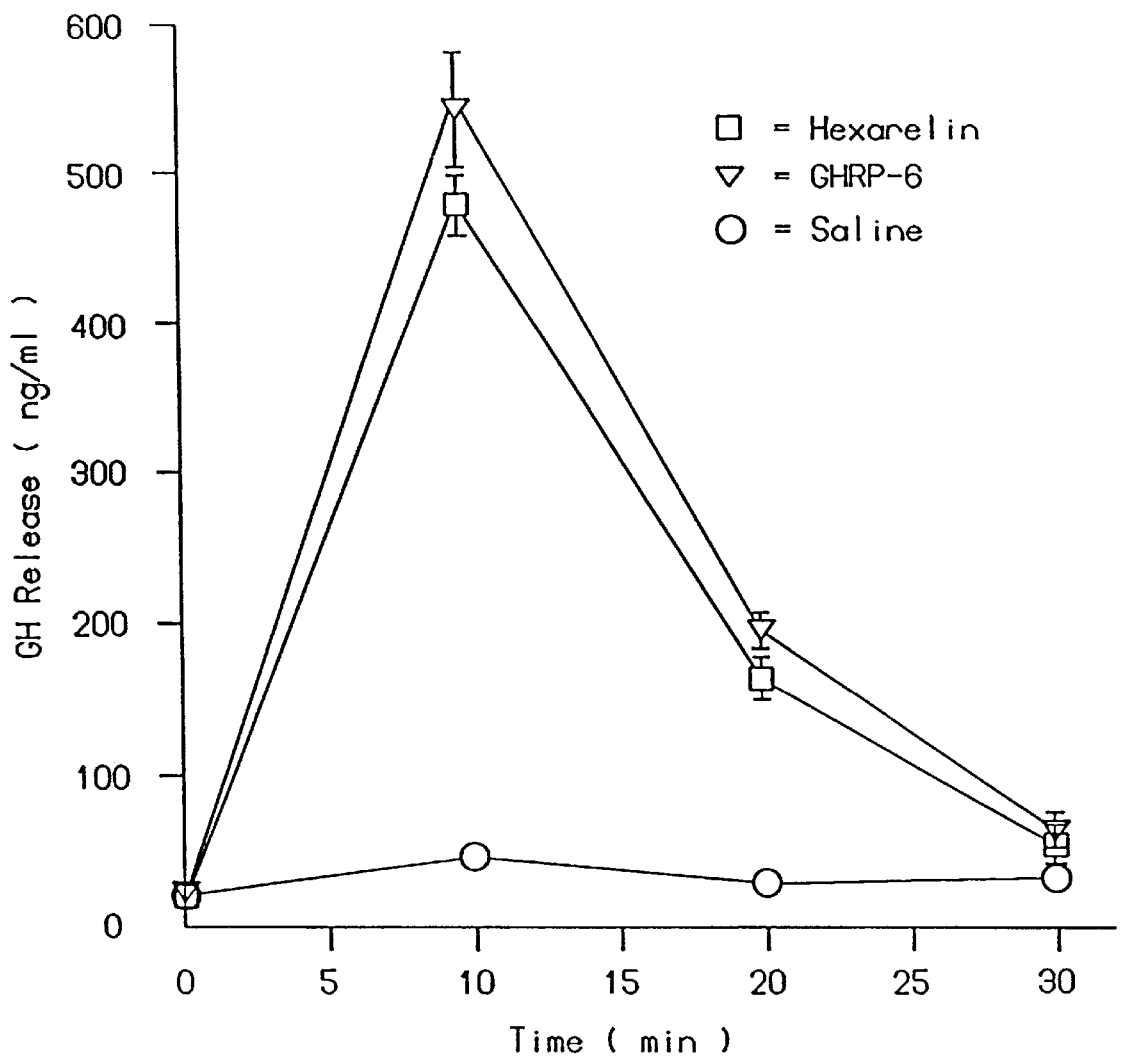

These data are also illustrated in FIGS. 3–5.

Potency and time-course of the effects of the two peptides were almost superimposable. In anesthetized rats, subcutaneous administration of HEXARELIN (150, 300 and 600 µg/kg) elicited a significant increase in plasma GH concentrations 10, 20 and 30 minutes after treatment. A similar profile of secretion was obtained after the administration of GHRP-6 at the same dose levels, as shown in Table 3. In this instance HEXARELIN appeared more effective than GHRP-6 at all the considered times. In all, both peptides after subcutaneous administration elicited a more prolonged stimulation of GH secretion although the maximum peak levels were considerably lower than those reported after intravenous injection.

TABLE 3

COMPARISON OF THE GH-RELEASING ACTIVITY OF
GHRP-6 (A) AND HEXARELIN (B) ADMINISTERED S.C.
IN MALE RATS ANESTHETIZED WITH KETAMINE AND XILAZINE

| TREATMENT | TIME (minutes) | | | |
|---|---|---|---|---|
| | 0 | 10 | 20 | 30 |
| Control | 26.0 ± 8.0(11) | 22.0 ± 3.3(8) | 59.2 ± 8.1(11) | 52.2 ± 5.5(11) |
| A 150 µg/kg | 20.0 ± 5.0(8) | 63.1 ± 11.0(8) | 110.4 ± 18.0(8) | 77.2 ± 14.0(8) |
| B 150 µg/kg | 12.0 ± 4.0(7) | 107.1 ± 17.7(7) | 156.6 ± 18.7(7) | 86.0 ± 18.9(7) |
| A 300 µg/kg | 20.0 ± 6.0(8) | 63.9 ± 12.8(8) | 123.4 ± 14.6(8) | 87.7 ± 11.8(8) |
| B 300 µg/kg | 12.0 ± 4.0(7) | 80.6 ± 11.0(7) | 171.7 ± 22.0(7) | 102.7 ± 17.0(7) |
| A 600 µg/kg | 18.0 ± 4.0(10) | 93.1 ± 22.3(7) | 167.1 ± 14.7(10) | 107.8 ± 9.5(10) |
| B 600 µg/kg | 23.0 ± 6.0(10) | 90.7 ± 16.6(7) | 187.5 ± 15.4(10) | 115.3 ± 19.1(10) |

Values (ng/ml) are means±S.E.M.

Number of rats are shown in parentheses and refer to pooled data of 2–3 experiments in which similar data were obtained.

Figure 6:
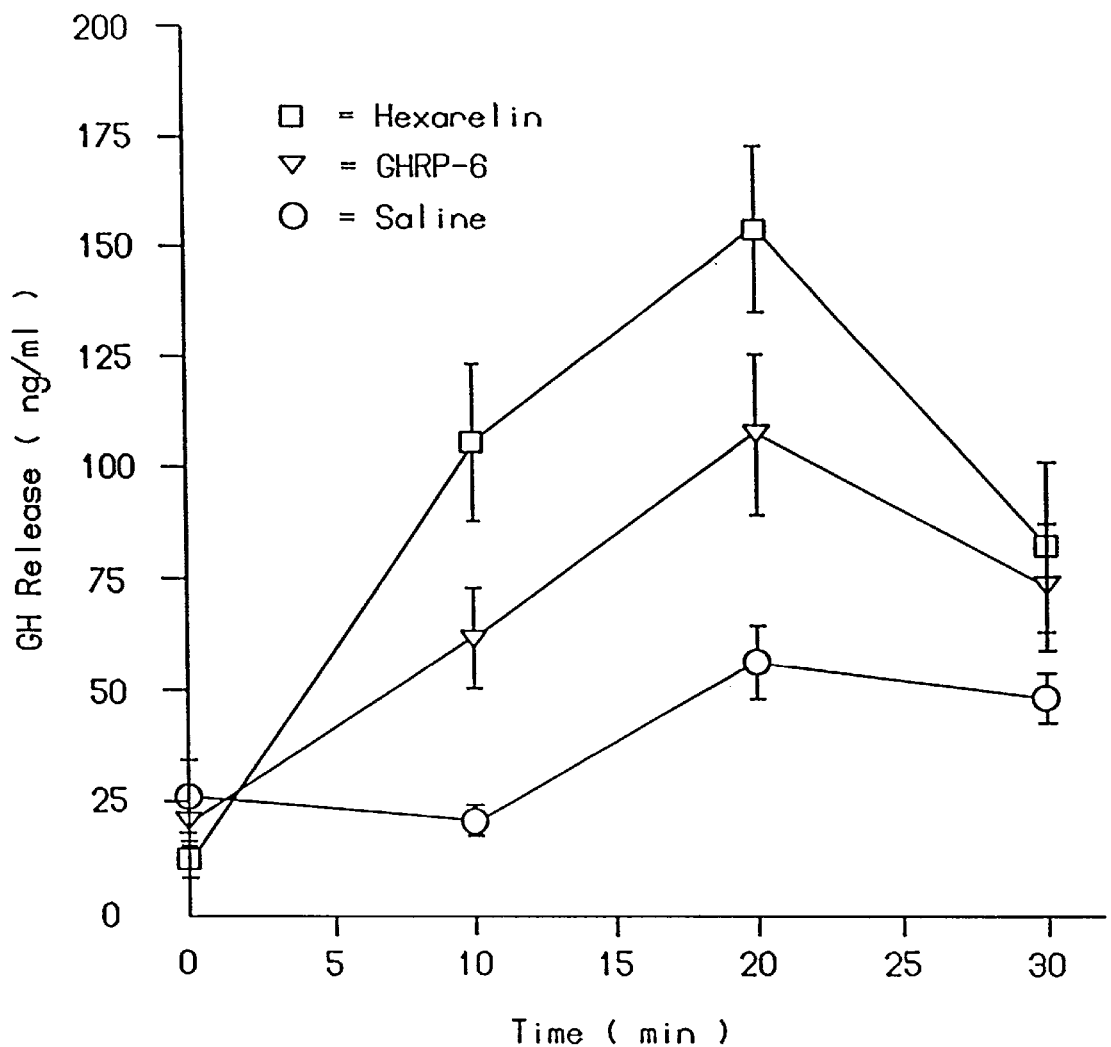
Figure 7:
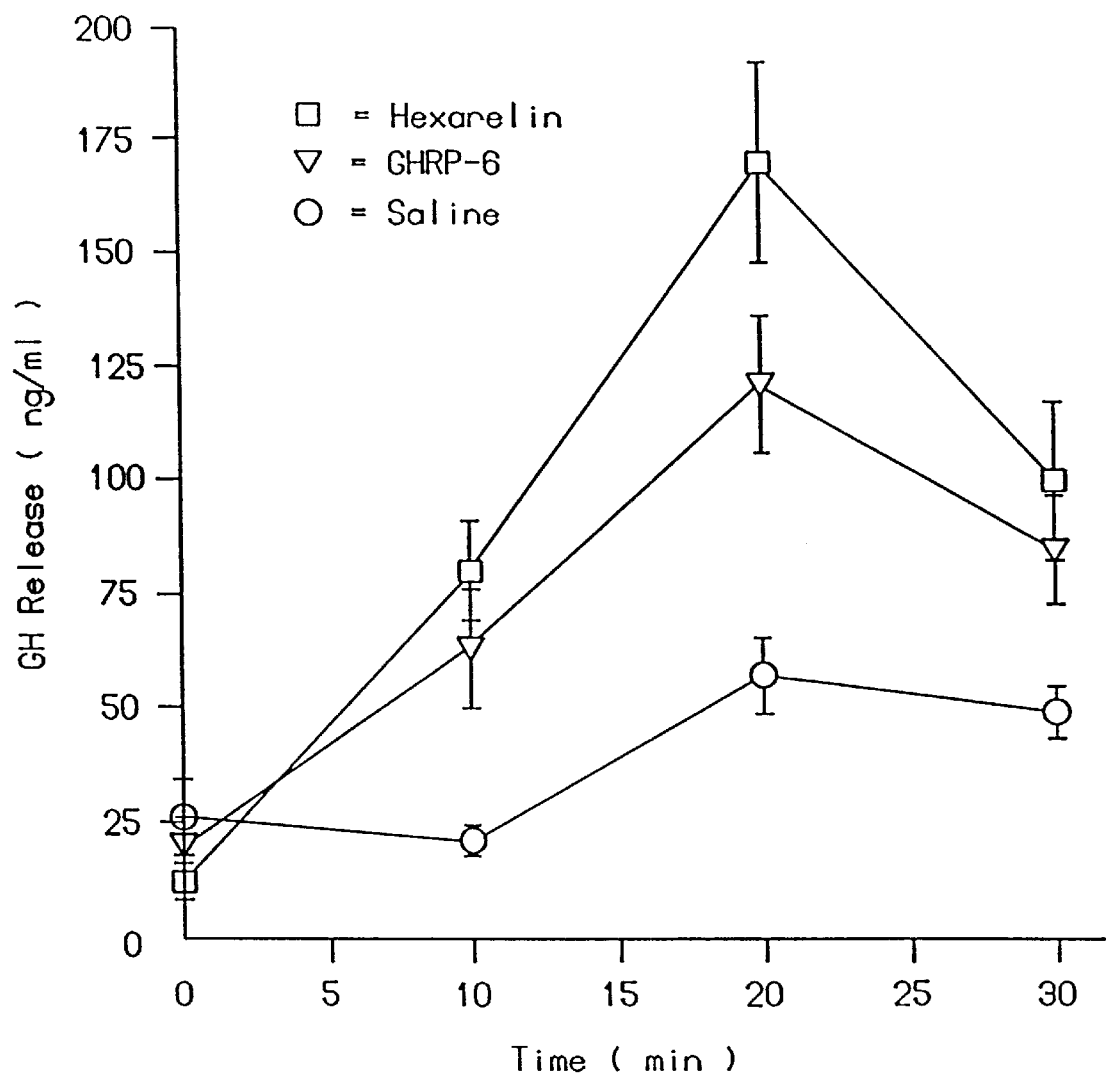
Figure 8:
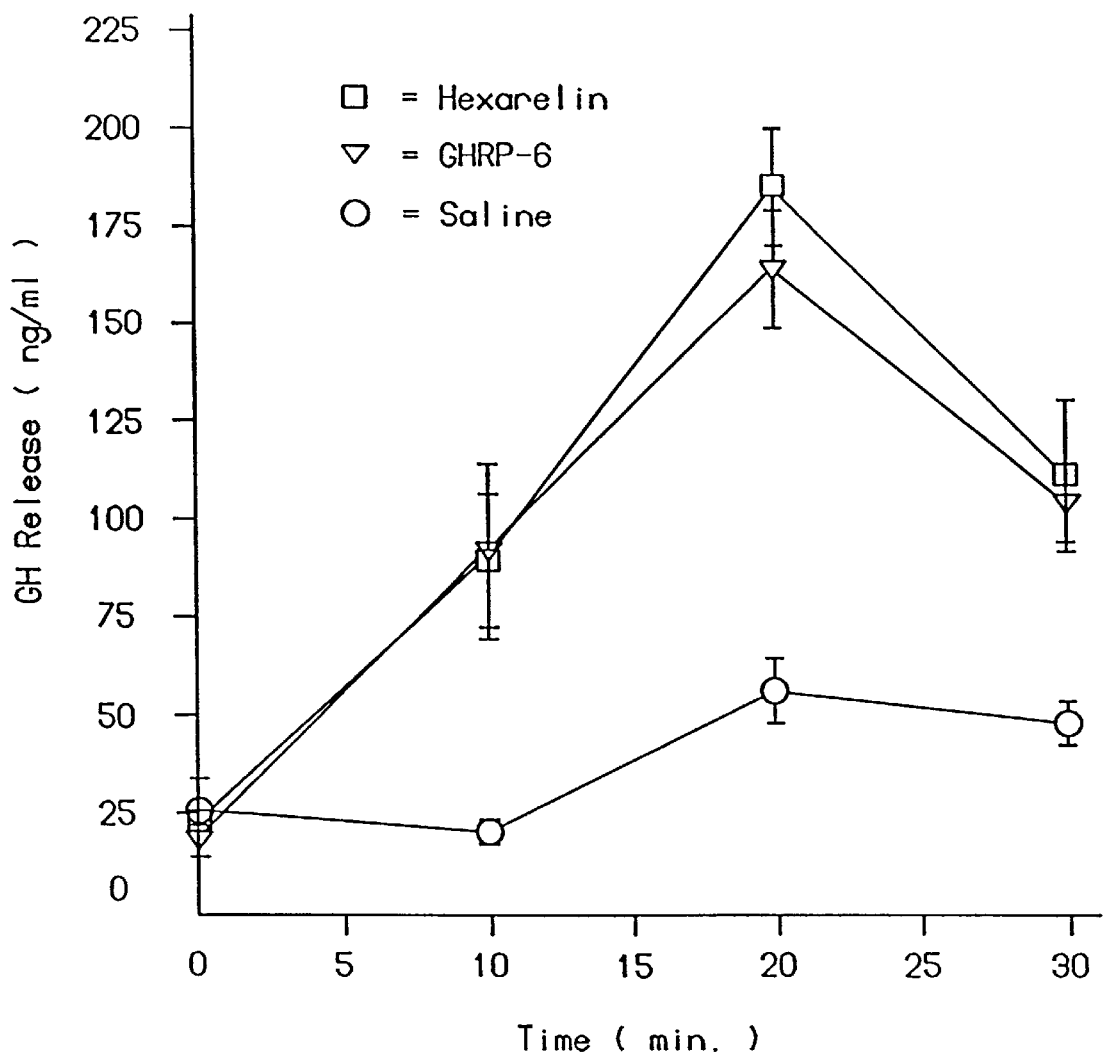

These data are also illustrated in FIGS. 6–8.

Example 11

Effect of HEXARELIN on GH Release in Pentobarbital-Anesthetized Rats

Male Sprague Dawley rats weighing 225–250 g were divided in groups of five animals each. Rats were anesthetized with Nembutal injected intraperitoneally at 50 mg/kg, fifteen minutes prior to the first blood withdrawal taken over heparin by cardiac puncture (for determination of basal GH).

Subcutaneous injections of either HEXARELIN or GHRP-6 were given immediately after the first blood collection, and additional blood samples were collected 15 and 40 minutes later.

Measurement of rat GH was performed by a standard double antibody radioimmunoassay with reagents supplied by the National Pituitary Agency and the National Institute of Arthritis, Diabetes, and Digestive and Kidney Diseases. The standards used were NIADDK-NIH-rGH-RP-2. Statistical data were obtained with the Student's t Test at a significance level of 5%. Results are shown in Table 4.

TABLE 4

COMPARATIVE EFFECT OF GHRP-6 AND HEXARELIN ON
GH RELEASE IN PENTOBARBITAL-ANESTHETIZED RATS
POST-DRUG PLASMA GH (ng/ml)

| COMPOUND | 0 min | 15 min | 40 min |
|---|---|---|---|
| Saline s.c. | 32 ± 15 | 43 ± 21 | 128 ± 38 |
| GHRP-6* | | | |
| s.c. | | | |
| 50 µg/kg | 57 ± 39 | 262 ± 58 | 97 ± 44 |
| 25 µg/kg | 41 ± 16 | 222 ± 95 | 110 ± 47 |

TABLE 4-continued

COMPARATIVE EFFECT OF GHRP-6 AND HEXARELIN ON
GH RELEASE IN PENTOBARBITAL-ANESTHETIZED RATS
POST-DRUG PLASMA GH (ng/ml)

| COMPOUND | 0 min | 15 min | 40 min |
|---|---|---|---|
| HEXARELIN | | | |
| s.c. | | | |
| 50 µg/kg | 32 ± 16 | 439 ± 69** | 81 ± 13 |
| 25 µg/kg | 56 ± 21 | 388 ± 99* | 100 ± 51 |
| 10 µg/kg | 63 ± 58 | 95 ± 44 | 88 ± 29 |

Student's t test: * 1% P 5% ** 0.1% P 1%

Statistical values obtained for HEXARELIN at 50 µg/kg and 25 µg/kg are compared to GHRP-6 at the same concentrations.

Figure 9:
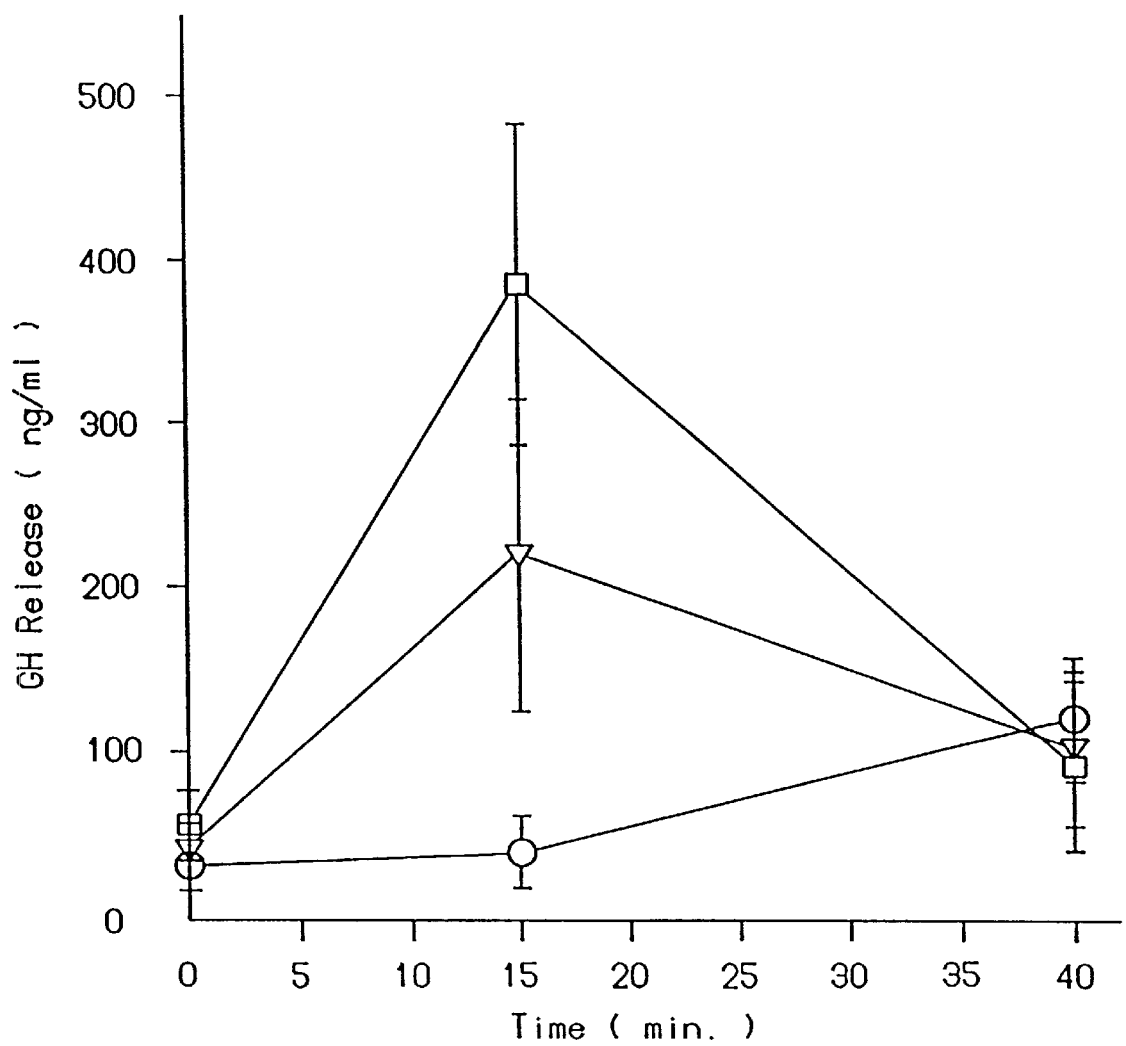
Figure 10:
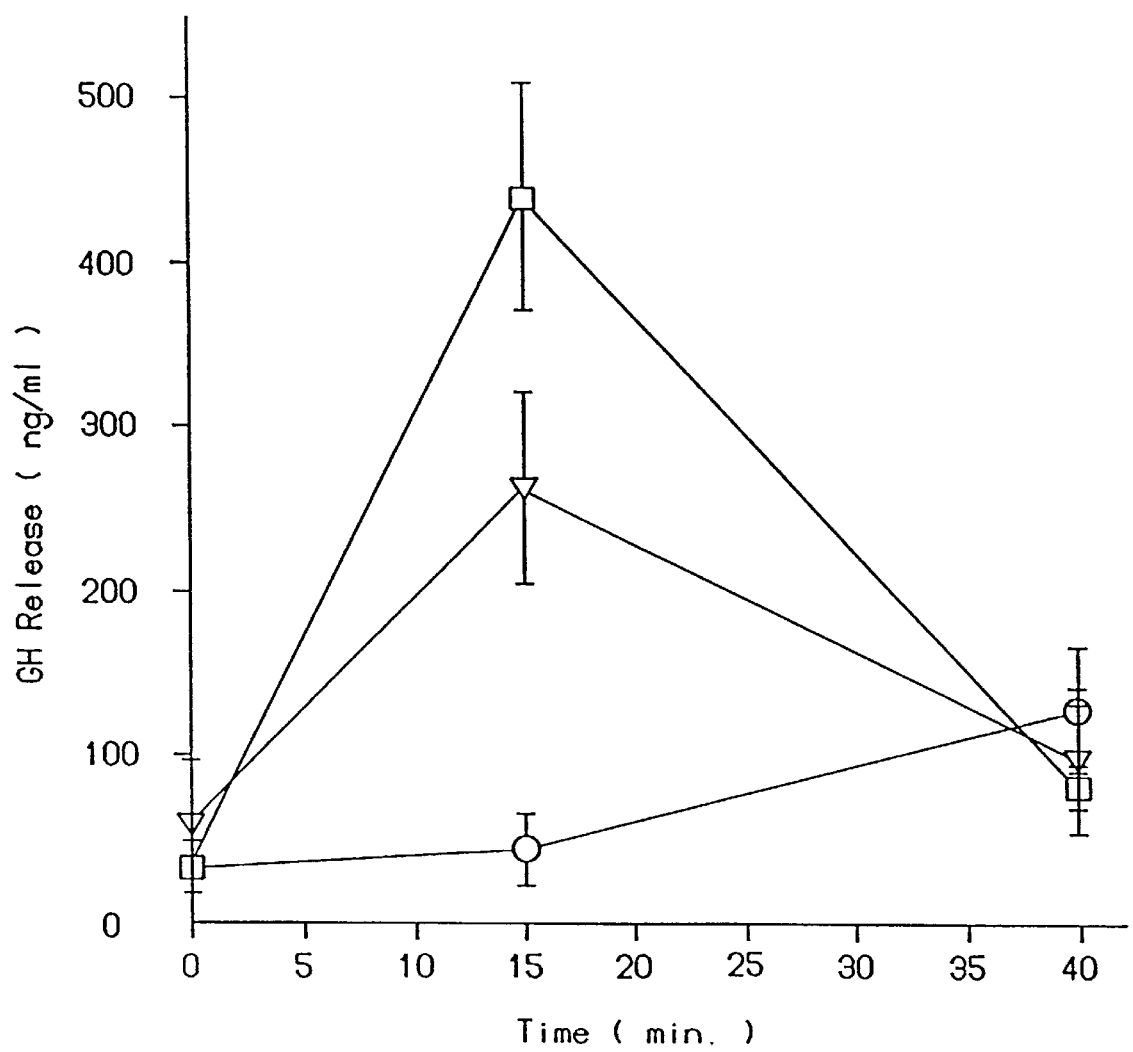
Figure 12:
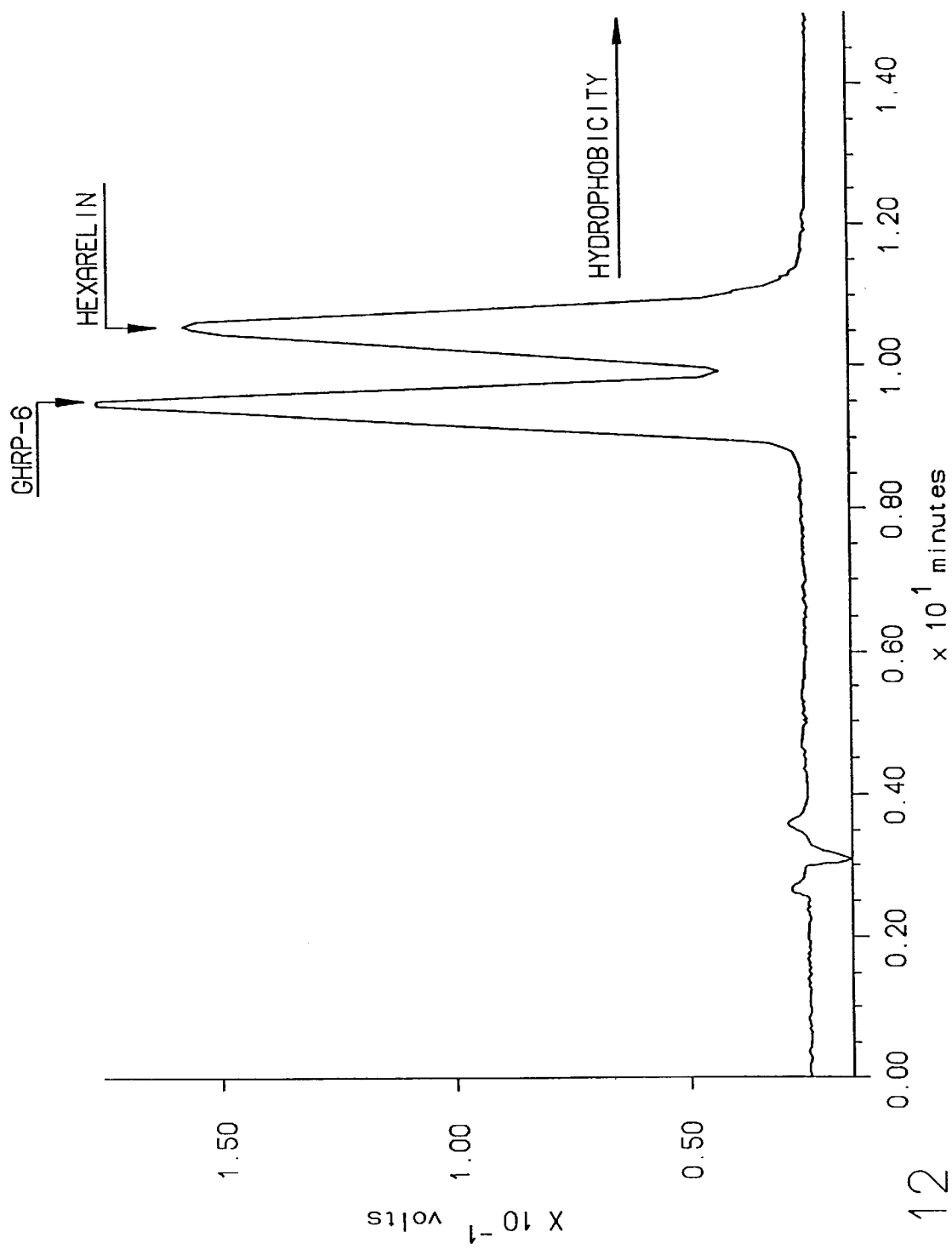
FIG. 12 is a graphical comparison of the hydrophobicity of GHRP-6 and HEXARELIN.

These data are also illustrated in FIGS. 9–11. Also, FIG. 12 illustrates that HEXARELIN has greater hydrophobicity than GHRP-6.

Example 12

These two peptides were also tested for acute cardiovascular toxicity in the rat.

| | HEXARELIN | | |
|---|---|---|---|
| GROUP | DOSE (mg/Kg) (*) | | NO. OF ANIMALS |
| 1 | 5 | | 6 |
| 2 | 7.5 | | 6 |
| 3 | 10 | | 6 |

| | GHRP-6 | | |
|---|---|---|---|
| GROUP | DOSE (mg/Kg) ($) | | NO. OF ANIMALS |
| 4 | 2.5 | | 6 |
| 5 | 5 | | 6 |
| 6 | 7.5 | | 6 |

(*) The dose levels of HEXARELIN were established by the Sponsor on the basis of a previous toxicity study.

-continued ($) The dose levels of GHRP-6 were established by the Sponsor on the basis of literature data (Macia R.A. et al., Toxicol. Appl. Pharm. 194, 403–410, 1990).

Dosages were calculated on the basis of the declared peptide content in each product, as specified below:

1) HEXARELIN: peptide content 79%
2) GHRP-6: peptide content 64%

A single dose of HEXARELIN or GHRP-6 was administered to rats in different calendar dates in such a way that each group/dose should be treated in two subsequent days.

Initially 3 rats/group/compound, the first ones in numerical order, were treated.

The treatment schedule was as follows:

| DAYS:  | 1       | 2       | 3       | 4        | 5        | 6        |
|--------|---------|---------|---------|----------|----------|----------|
| Groups | 3 and 4 | 3 and 4 | 1 and 5 | 1 and 5  | 2 and 6  | 2 and 6  |
| Cages  | 5 and 7 | 6 and 8 | 1 and 9 | 2 and 10 | 3 and 11 | 4 and 12 |

For each compound, appropriate amounts of solutions in 0.9% NaCl for injection were prepared just before treatment at the suitable concentrations. The solutions were sterilized by filtration (Millipore filter, pore size 0.22 μm). Owing to the type of the study (acute study) in which formulates were administered just after preparation, stability checks were not performed. Concentration checks were also not performed. The volume of solution injected was maintained constant at 1 ml/Kg.

The intravenous injections were done as a single dose in one vein of the tail with an appropriately gauged sterile, disposable, plastic syringe. The injection rate was about 0.1 ml/sec.

Periodical observations were made up to 4 hours after treatment. Abnormality and mortality were recorded. Body weight was recorded once during pre-trial and on the administration day to calculate the volumes to be injected.

The mortality data obtained with the two products were:

| Dose       | Dead rats/Total N° of rats per group |
|------------|--------------------------------------|
| GHRP-6     |                                      |
| 2.5 mg/kg  | 0/6                                  |
| 5.0 mg/kg  | 1/6                                  |
| 7.5 mg/kg  | 2/6                                  |
| HEXARELIN  |                                      |
| 5.0 mg/kg  | 0/6                                  |
| 7.5 mg/kg  | 1/6                                  |
| 10 mg/kg   | 2/6                                  |

The results indicate that HEXARELIN shows the same lethality as GHRP-6 but consistently at a higher dose, i.e., it is less toxic than GHRP-6, an unexpected finding particularly since HEXARELIN is more potent regarding its pharmacological activity.

Example 13

Stability of HEXARELIN Compared to GHRP6 After Irradiation in Solution

Solutions of Hexarelin and GHRP-6 in acetate buffer pH 5.4 (1 mg/ml w/v) were submitted to irradiation (Co 60) at doses varying from 0 to 1.6 MRad with intervals of 2 MRad.

Subsequently, the samples were analyzed by RP-HPLC using 27% Acetonitrile in water as solvent, and the area of the peptide peak was examined.

The figure shows the variation of the percentage of residual material according to the irradiation dose:

$$\left[\frac{\text{Peak area for dose } X}{\text{Peak area of control}} \times 100\right]$$

Figure 13:
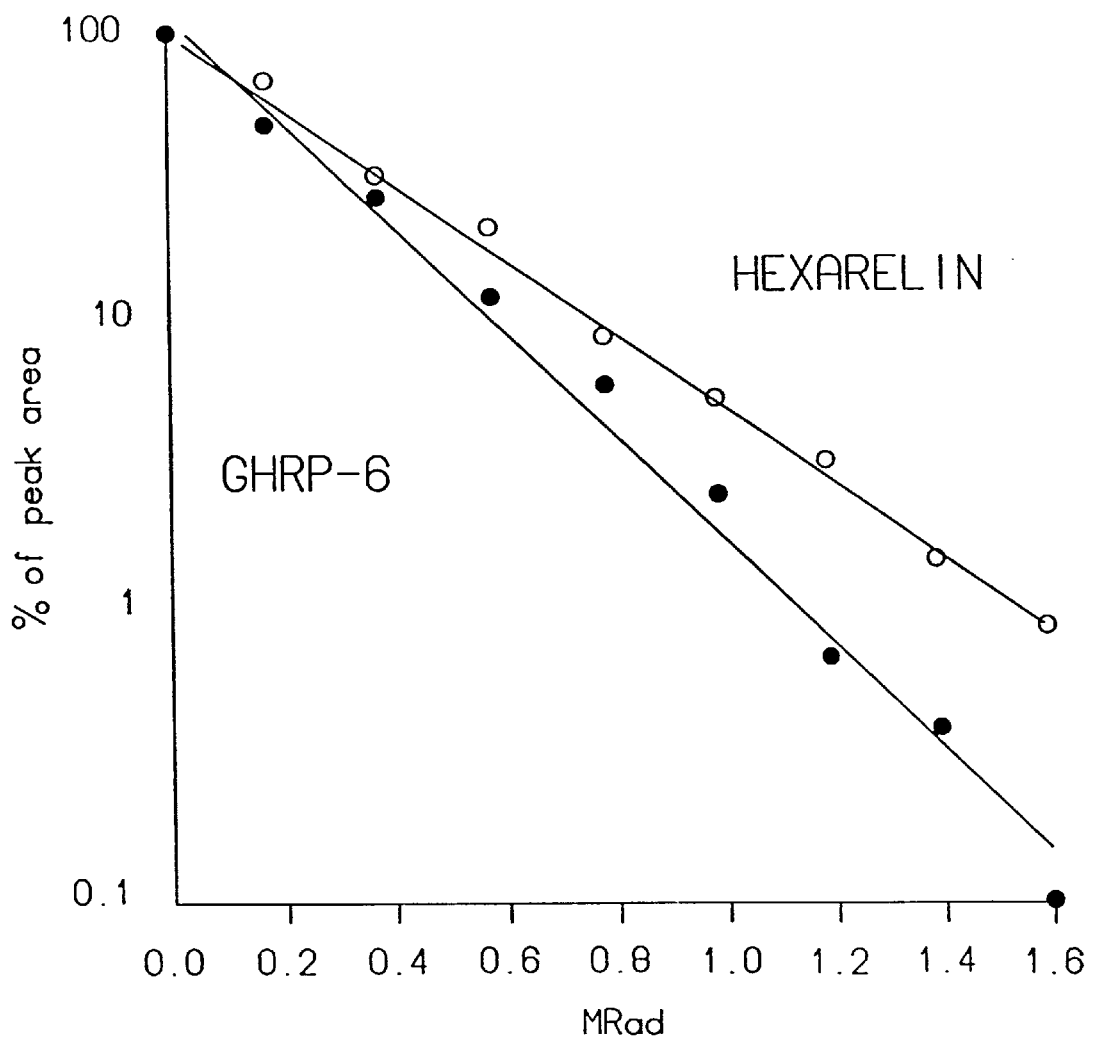
FIG. 13 is a graphical representation of the effect of irradiation on GHRP-6 and HEXARELIN in an acetate buffer solution.
Figure 14A:
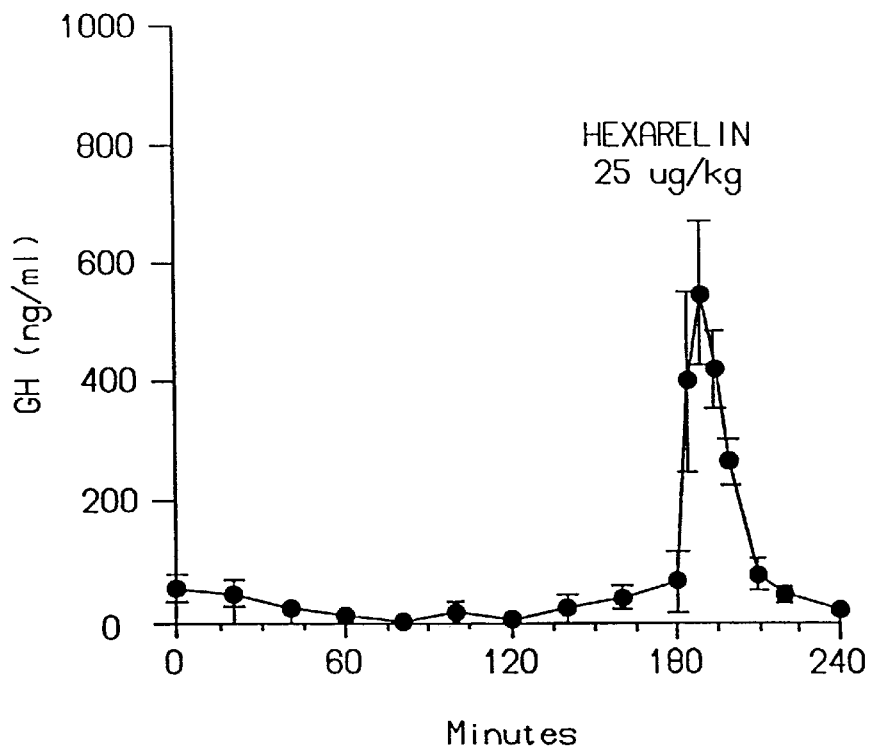
FIGS. 14a, 14b, 15a, 15b, 16a, 16b, 17a, 17b are graphical representations of GH release in anesthetized male rats following intravenous administration of saline, GHRP-6 and HEXARELIN.
Figure 14B:
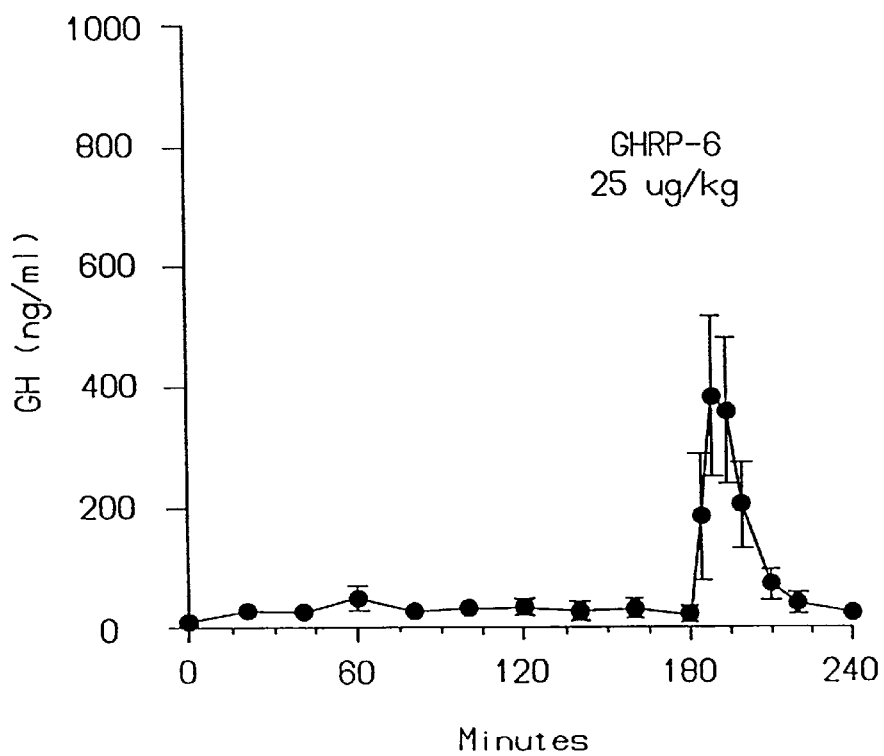
Figure 15A:
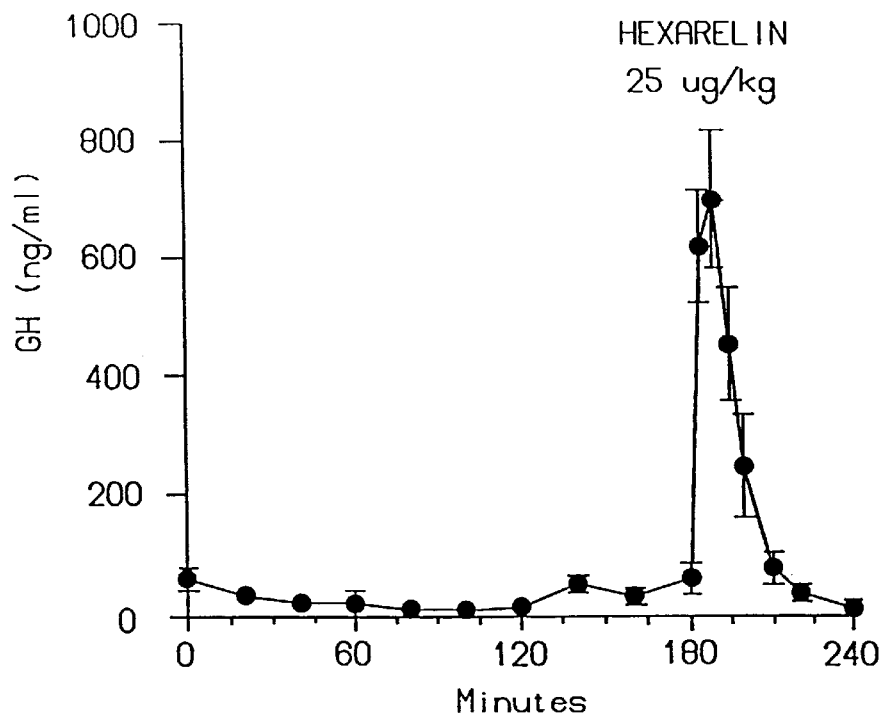
Figure 15B:
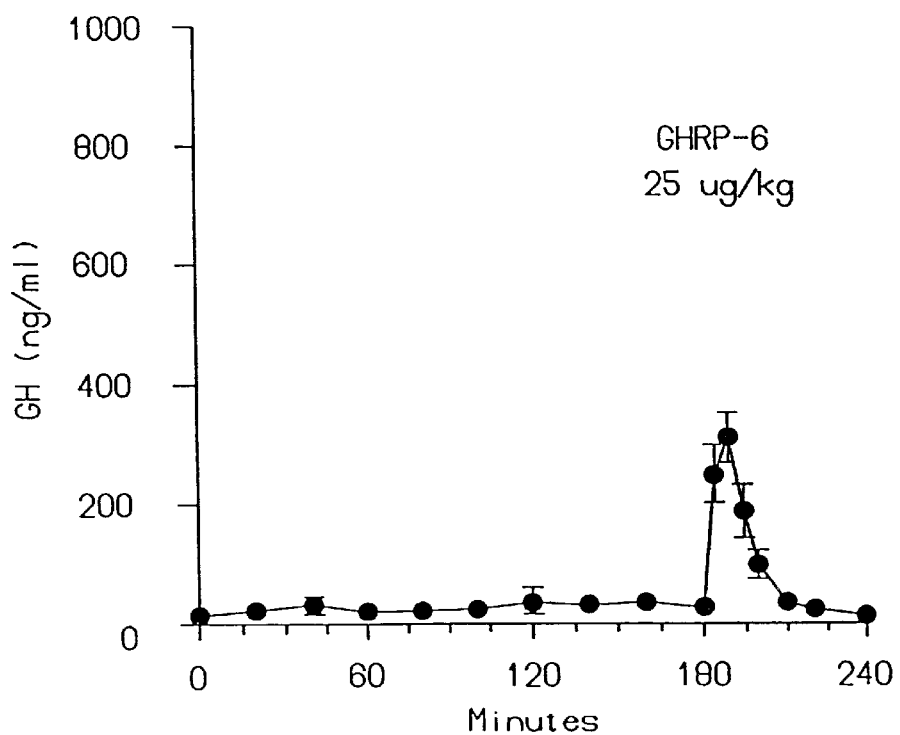
Figure 16A:
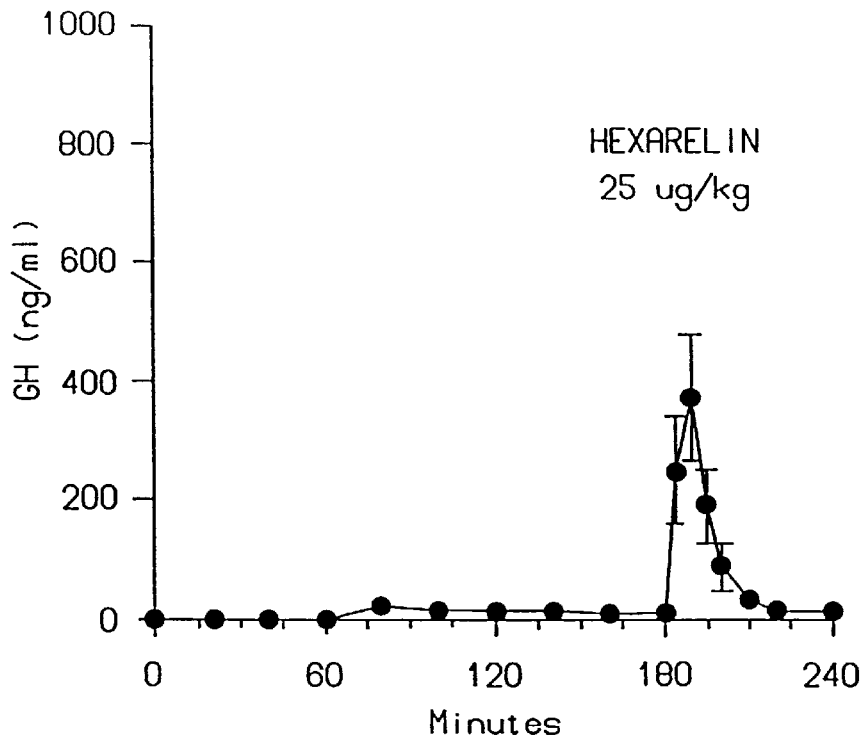
Figure 16B:
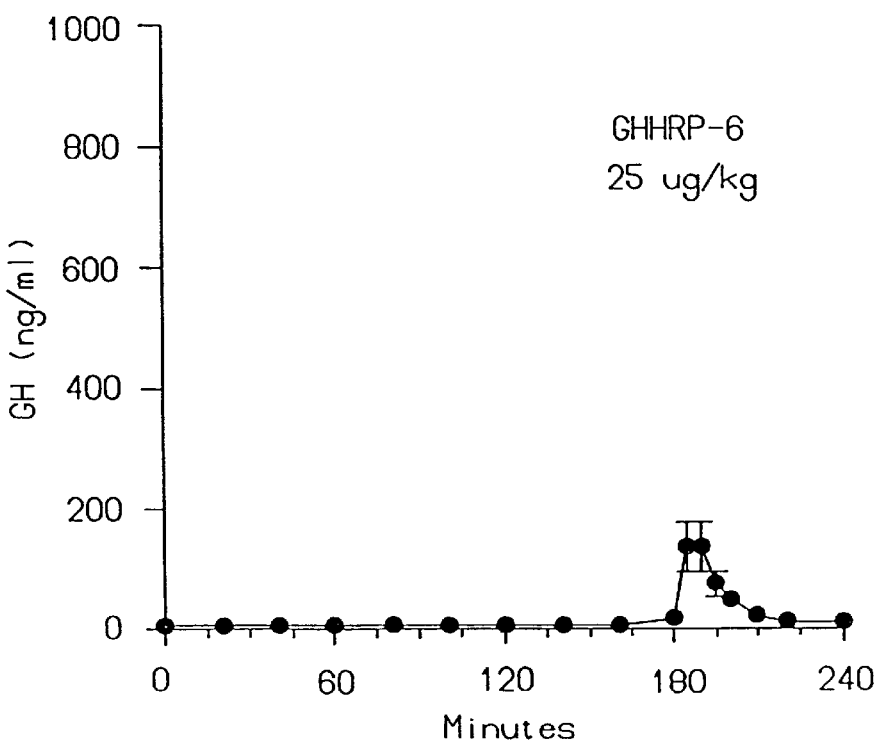
Figure 17A:
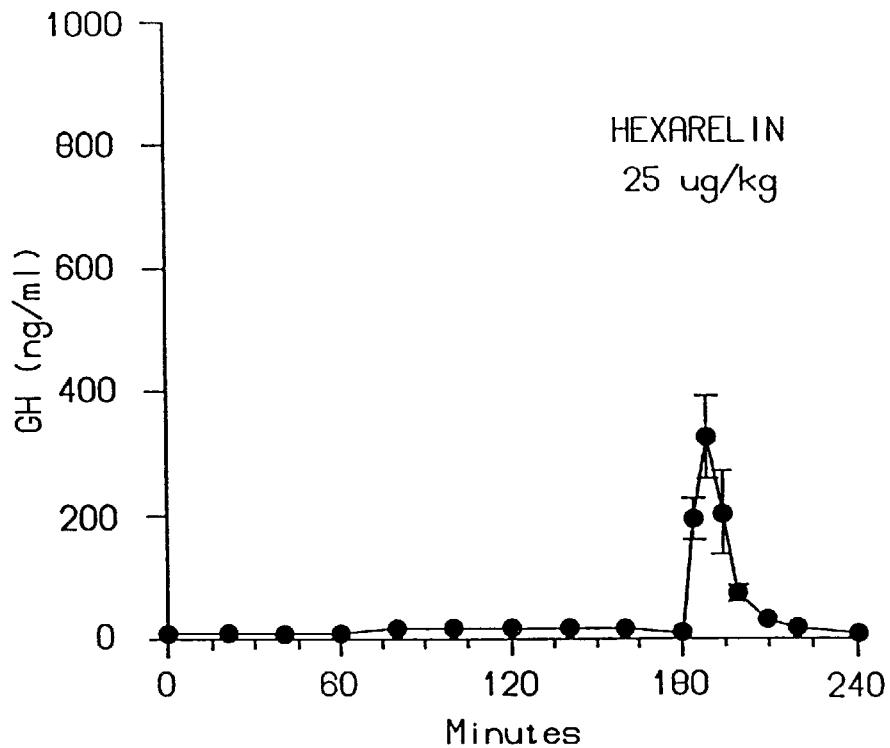
Figure 17B:
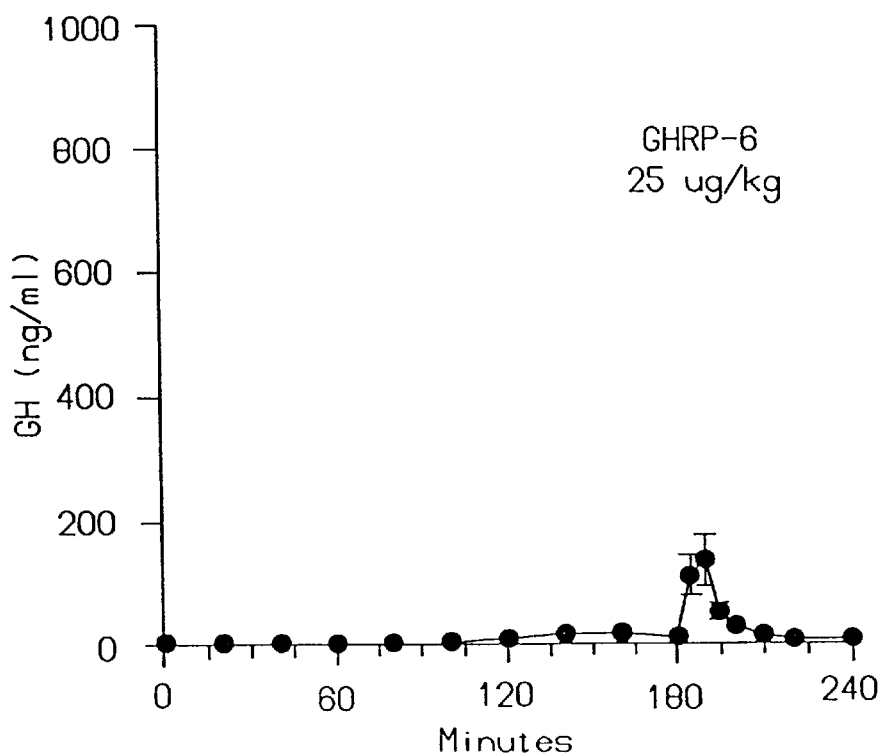
Figure 18:
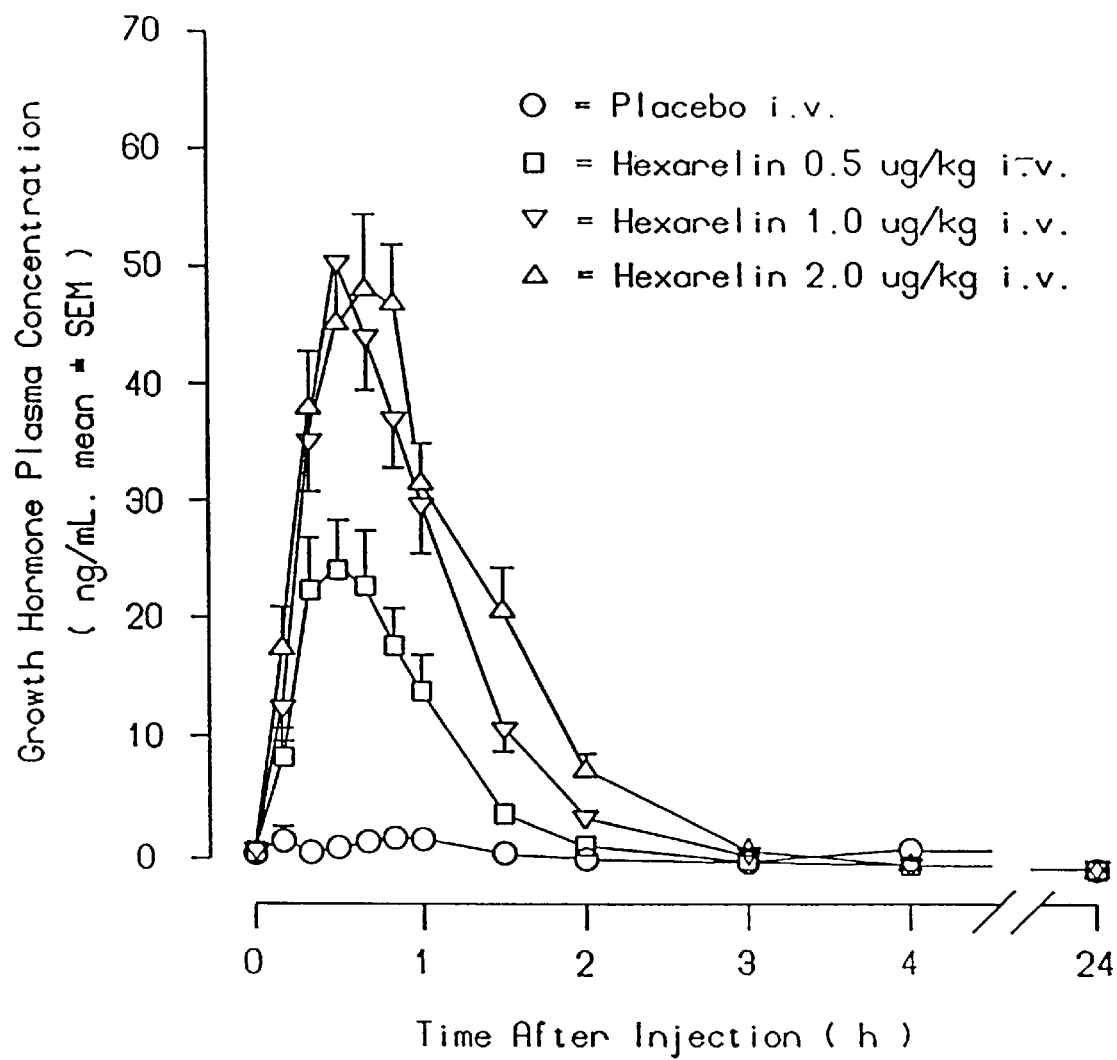
FIGS. 18–20 are graphical representations of the effect of HEXARELIN on growth hormone secretion in young healthy male volunteers.
Figure 19:
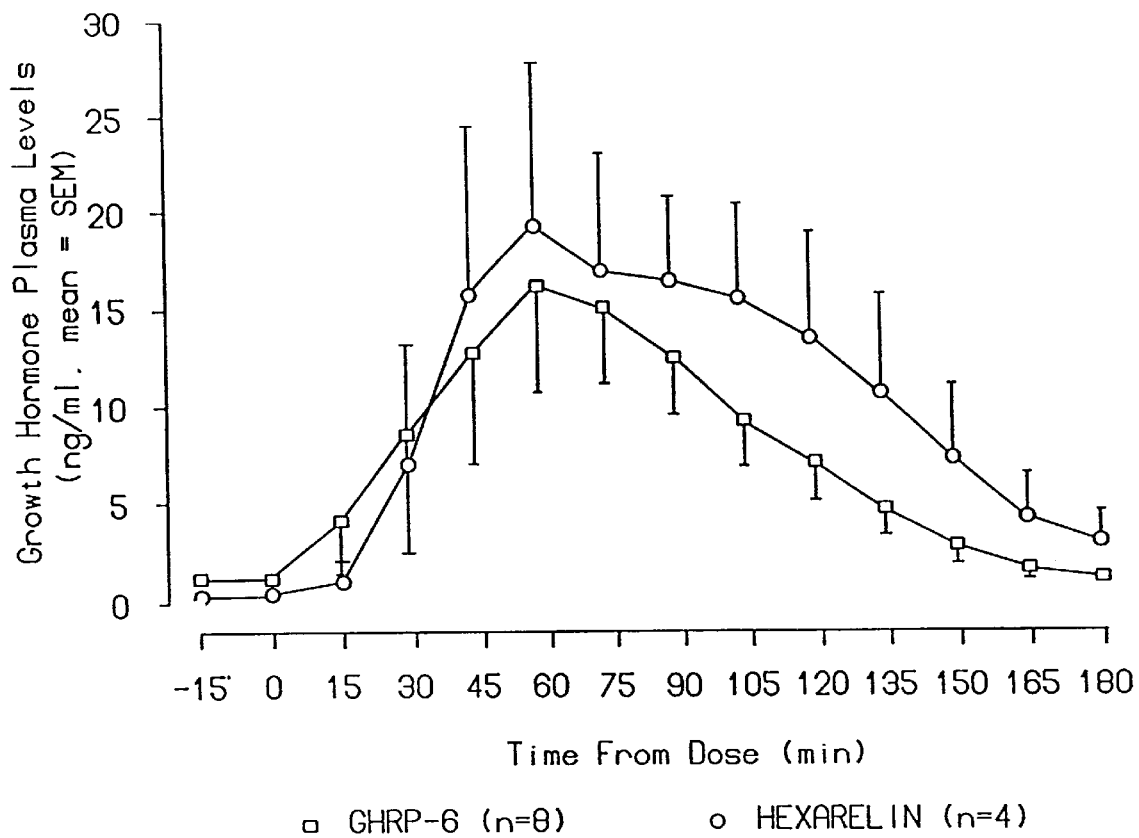

Results are shown in FIG. 13.

Example 14

In this example, the neuroendocrine mechanism by which HEXARELIN and GHRP-6 mediate their actions has been compared. Although previous studies have looked at the role of somatostatin in regulating the action of GHRP-6 in culture and in stressed animals, this study observes the role of both somatostatin and GHRH in regulating the action of HEXARELIN and GHRP-6 in conscious, freely-moving, nonstressed animals.

Sixty male rats were prepared with indwelling venous catheters under ether anesthesia three days before experimentation. On the day of experimentation, all animals were given an iv heparin injection (100 IU; 0630 h). At 0700 h, animals were treated with 0.5 ml of either normal serum (control-as), somatostatin antiserum (somatostatin-as; 0.25 ml+0.25 ml saline), growth hormone-releasing hormone antiserum (GHRH-as; 0.25 ml+0.25 ml saline), or both somatostatin antiserum and growth hormone-releasing hormone antiserum (0.25 ml somatostatin-as+0.25 ml GHRH-as). Blood sampling began 60 minutes after antiserum pretreatment, with blood samples collected every 20 minutes for three hours. After the 180 minute sample (1100 h), animals were treated iv with 25 μg/kg of either Hexarelin or GHRP-6. Blood samples were then collected at 5, 10, 15, 20, 30, 40, and 60 minutes after peptide treatment. All samples were centrifuged immediately and the plasma frozen until assayed. The peak GH response to Hexarelin and GHRP-6 as well as the area under the response curves (AUCs) for the thirty minutes following peptide injection were calculated. Data were subjected to repeated measures analysis of variance and are expressed as mean±SEM.

Factorial analysis of variance identified several main treatment effects.

A. Peptide Effects: The pooled results obtained from treatment with either HEXARELIN or GHRP-6 suggest that, overall, HEXARELIN was more effective in eliciting a higher mean GH response as compared to GHRP-6, as shown in Table 5. GH AUC and peak GH responses were also significantly higher.

B. Antisera Effects: Antisera pretreatment clearly demonstrated that GHRH antiserum inhibited the GH response to both Hexarelin and GHRP-6. The mean GH response was significantly inhibited in GHRH antiserum pretreated rats as compared to animals which were not pretreated (Table 6). The GH AUC and peak GH responses were significantly diminished.

TABLE 5

Main Treatment Effects

| Peptides  | Mean GH (ng/ml) | GH AUC (ng/ml/30 min) | Peak GH (ng/ml) |
|-----------|-----------------|-----------------------|-----------------|
| Hexarelin | 235 ± 21**      | 7366 ± 912**          | 552 ± 59**      |
| GHRP-6    | 131 ± 13        | 4220 ± 665            | 293 ± 41        |

TABLE 5-continued

Main Treatment Effects

| Peptides | Mean GH (ng/ml) | GH AUC (ng/ml/30 min) | Peak GH (ng/ml) |
|---|---|---|---|
| Antiserum (as) | | | |
| control-as | 241 ± 31 | 7716 ± 1457 | 5#4 ± 97 |
| somatostatin-as. | 224 ± 23 | 7011 ± 1603 | 516 ± 63 |
| GHRH-as. | 116 ± 18## | 3771 ± 924## | 288 ± 69# |
| somatostatin-as + GHRH-as | 98 ± 14# | 3021 ± 565## | 249 ± 46# |

**(p < 0.01) significantly higher than GHRP-6 treated animals.
(p < 0.01), ##(p < 0.05) significantly lower than control and somatostatin-as pretreated animals.

The responses of the individual treatment groups are also illustrated in FIGS. 15 to 19.

This Example investigated what role GHRH and somatostatin have in the neuroendocrine mechanism by which the GHRPs, HEXARELIN and GHRP-6, mediate their neuroendocrine effects. In vitro studies have suggested that the GHRPs exert an effect via a direct pituitary site of action. Here, however, the administration of HEXARELIN as well as GHRP-6 to conscious, freely-moving (non-stressed) animals, suggests that GHRH is integrally involved in the mechanism by which HEXARELIN and GHPR-6 mediate their GH-releasing effects in vivo. This corroborates an earlier study in acutely-treated, stressed animals where passive immunization of endoqenous GHRH resulted in a diminished plasma GH diminished plasma GH response to GHRP-6.

It has previously been suggested that somatostatin is involved in the mechanism by which GHRP-6 mediates its neuroendocrine effects. This was an acute study, however, conducted in a fashion known to induce stress, and thus, increase somatostatin tone in rats. In contrast, the results of the present study suggest minimal somatostatin involvement. We find these results surprising, both in light of the previous study and since we have found somatostatin to be involved in most GH-releasing mechanisms previously examined. The apparent disparity in results between the two studies may be accounted for by the fact that we performed our study in non-stressed, conscious, freely-moving rats. In such non-stressed animals, somatostatin tone is variable: low during a GH peak, or high may underestimate the importance of somatostatin in this mechanism. For these reasons, we are hesitant to exclude the involvement of somatostatin at this time and feel that further analysis of somatostatin's involvement is warranted.

Example 15

Figure 20:
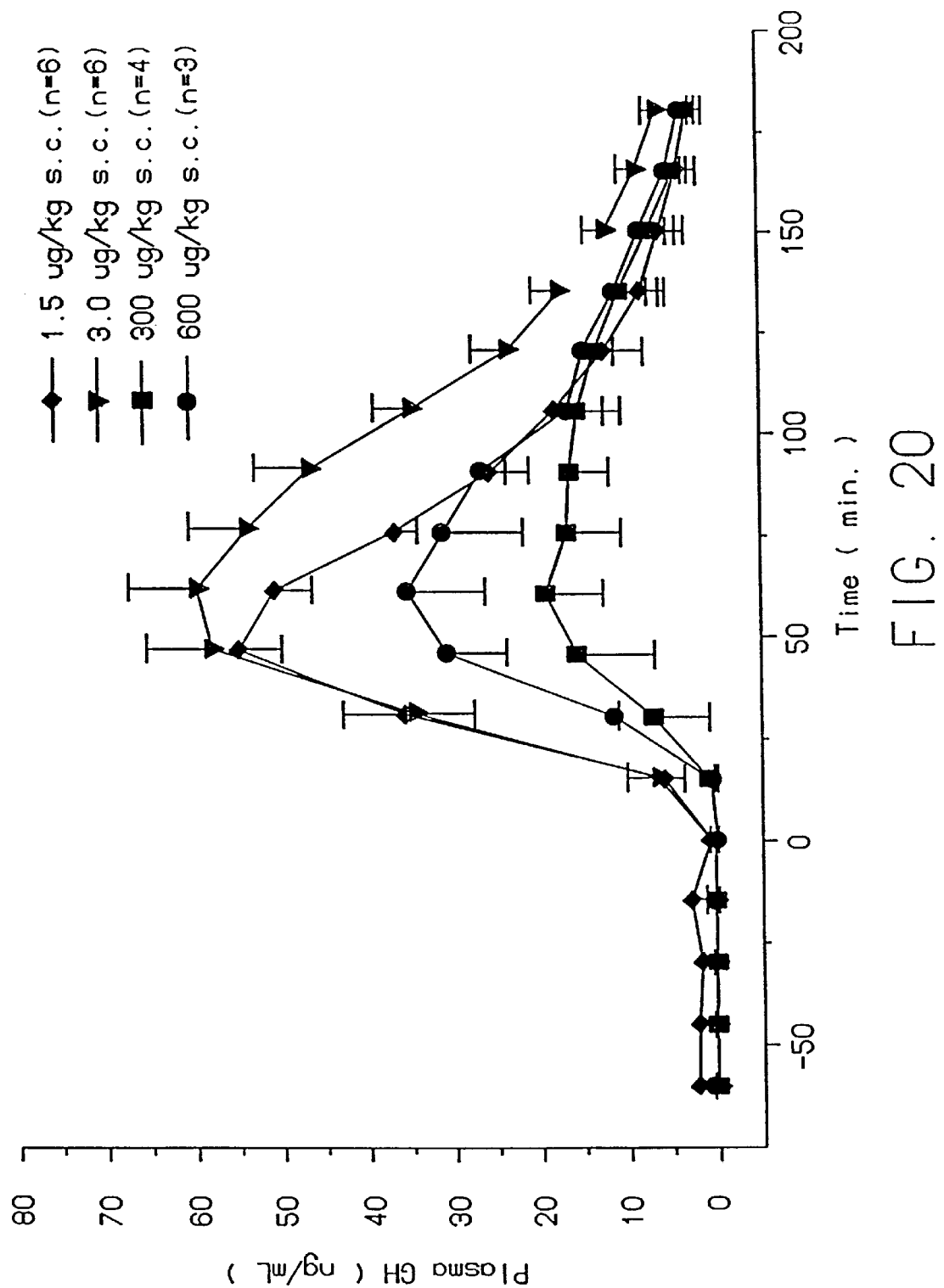

The effects of HEXARELIN on growth hormone secretion in young (20–30 years old) healthy male volunteers were measured after the administration of various dosages. The results shown in FIGS. 18–20 demonstrate that the peptide is effective in vivo as well as in vitro.

Example 16

The peptide of Example 3 was formulated in a polymeric PLGA implant in the form of rods which were about 1 cm long and 1 mm in diameter. These implants contained a loading of either 20 or 25% of the peptide (an amount of 7 or 10 mg), and were inserted subcutaneously into in male Beagle dogs which weighed between 10 and 12 kg. After an initial flare-up, plasma testosterone fell below castration levels after approximately 10 days, and was maintained for approximately 180 days. The absence of response after a stimulation by i.v. administration of the peptide at day 145 indicates down-regulation of the pituitary receptors. No clinical side effects were observed during this study.

Although the aforementioned examples of the present invention disclose specific embodiments thereof, it is believed that the substitution of an D-2-alkylTryptophan in bioactive peptides which contain at least one Tryptophan residue will yield bioactive peptides providing the advantages and benefits discussed above.

The incorporation of a D-2-alkylTryptophan in bioactive peptides as described above provides a method for prolonging and preserving the activity of such peptides. When analogous bioactive peptides not substituted with an D-2-alkylTryptophan are exposed to various processing conditions and substances, the activity of such peptides may be adversely effected. Sterilizing procedures used in the pharmaceutical industry may expose bioactive compounds to ionizing radiation. Such radiation may effect the formation of reactive radicals. Tryptophan containing peptides are particularly susceptible to attack by such radicals and such attack may render the peptide ineffective, or possibly toxic.

Furthermore, various formulating compounds, such as polylactic-polyglycolic acid (PLGA) polymers may contain active, or activated groups which may also attack Tryptophan containing bioactive peptides. The present invention provides a method for protecting a tryptophan containing bioactive peptide from these manufacturing hazards while also increasing the peptides resistance to oxidative degradation after formulation is complete. It is believed that the presence of the alkyl group at the number 2 position of the Tryptophan increases the stability of the pyrrole ring wherein attack by reactive radicals and active or activated groups occurs.

Example 17

Making use of the solid-phase peptide synthesis technique as described in "Solid phase peptide synthesis" by E. Atherton and R. C. Sheppard, IRL Press, Oxford University Press, 1984, using fluorenylmethoxycarbonyl (Fmoc) as the protecting group, the peptide:

GAB-D-2-Mrp-D-2-Mrp-Phe-Lys-NH$_2$, was prepared, wherein Mrp is 2-methyltryptophan, M.W. 779.9, found 778.4; purity (HPLC) 98.0%

Example 18

Analogously to Example 17, the following peptide was prepared: GAB-D-2-Mrp-D-2-Mrp-2-Mrp-Lys-NH$_2$, wherein Mrp is 2-methyltryptophan, M.W. 830.8, found 831.3; purity (HPLC) 98.0%.

Example 19

Analogously to Example 17, the following peptide was prepared: Aib-D-2-Mrp-D-2-Mrp-NH$_2$, wherein Mrp is 2-methyltryptophan, M.W. 502.6, found 503.3; purity (HPLC) 99.0%.

Example 20

Analogously to Example 17, the following peptide was prepared: Aib-D-2-Mrp-2-Mrp-NH$_2$, wherein Mrp is 2-methyltryptophan, M.W. 502.6, found 503.3; purity (HPLC) 99.0%.

Example 21

Analogously to Example 17, the following peptide was prepared: Aib-D-Ser(Bzl)-D-Mrp-NH$_2$,
wherein Mrp is 2-methyltryptophan, M.W. 479.6, found 480.5; purity (HPLC) 99.0%.

Example 22

Analogously to Example 17, the following peptide was prepared: GAB-D-2-Mrp-D-βNal-Phe-Lys-NH$_2$,
wherein 2-Mrp is 2-methyltryptophan, M.W. 774.8, found 775: purity (HPLC) 99.0%.

Example 23

Analogously to Example 17, the following peptide was prepared: GAB-D-2-Mrp-D-2-Mrp-D-2-Mrp-Lys-NH$_2$,
wherein 2-Mrp is 2-methyltryptophan, M.W. 830.8, found 831.5: purity (HPLC) 99.0%.

Example 24

Analogously to Example 17, the following peptide was prepared: D-2-Mrp-D-2-Mrp-2-Mrp-NH$_2$,
wherein 2-Mrp is 2-methyltryptophan, M.W. 617.7, found 618.3: purity (HPLC) 99.0%.

Example 25

Analogously to Example 17, the following peptide was prepared: D-2-Mrp-2-Mrp-NH$_2$,
wherein 2-Mrp is 2-methyltryptophan, M.W. 417.5, found 418.3: purity (HPLC) 99.0%.

Example 26

Analogously to Example 17, the following peptide was prepared: GAB-D-2-Mrp-2-Mrp-NH$_2$,
wherein 2-Mrp is 2-methyltryptophan, M.W. 502.6, found 503.2: purity (HPLC) 99.0%.

Example 27

Biological Activity

In vivo activity of these compounds was determined in ten day-rats, which were subcutaneously injected (s.c.) with a dose of 300 μg/kg or with different doses in dose-response studies, according to methods described in detail by R. Deghenghi et al, *Life Sciences*, 54, 1321, (1994). The results are provided in Table 6 below. The released GH was measured after 15 minutes from the treatment.

TABLE 6

| Peptide of example | Dose μg/kg s.c. | released GH (ng/ml) |
|---|---|---|
| 17 | 300 | 155.4 ∓ 19.7 |
| 18 | 300 | 165.4 ∓ 18.5 |
| 19 | 300 | 174.2 ∓ 25.9 |
| 20 | 300 | 64.2 ∓ 12.6 |
| 21 | 1.2 mg/kg | 59.4 ∓ 12.3 |
| 22 | 300 | 145.7 ∓ 9.0 |
| 23 | 300 | 91.2 ∓ 9.0 |
| 24 | 300 | 26.3 ∓ 5.0 |
| 25 | 300 | 27.0 ∓ 4.8 |
| 26 | 300 | 36.0 ∓ 9.5 |
| Controls | — | 15.7 ∓ 6.7 |

The data shows that the peptides of Examples 17, 18, 19 and 23 are the most active.

Example 28

Figures 21A, 21B:
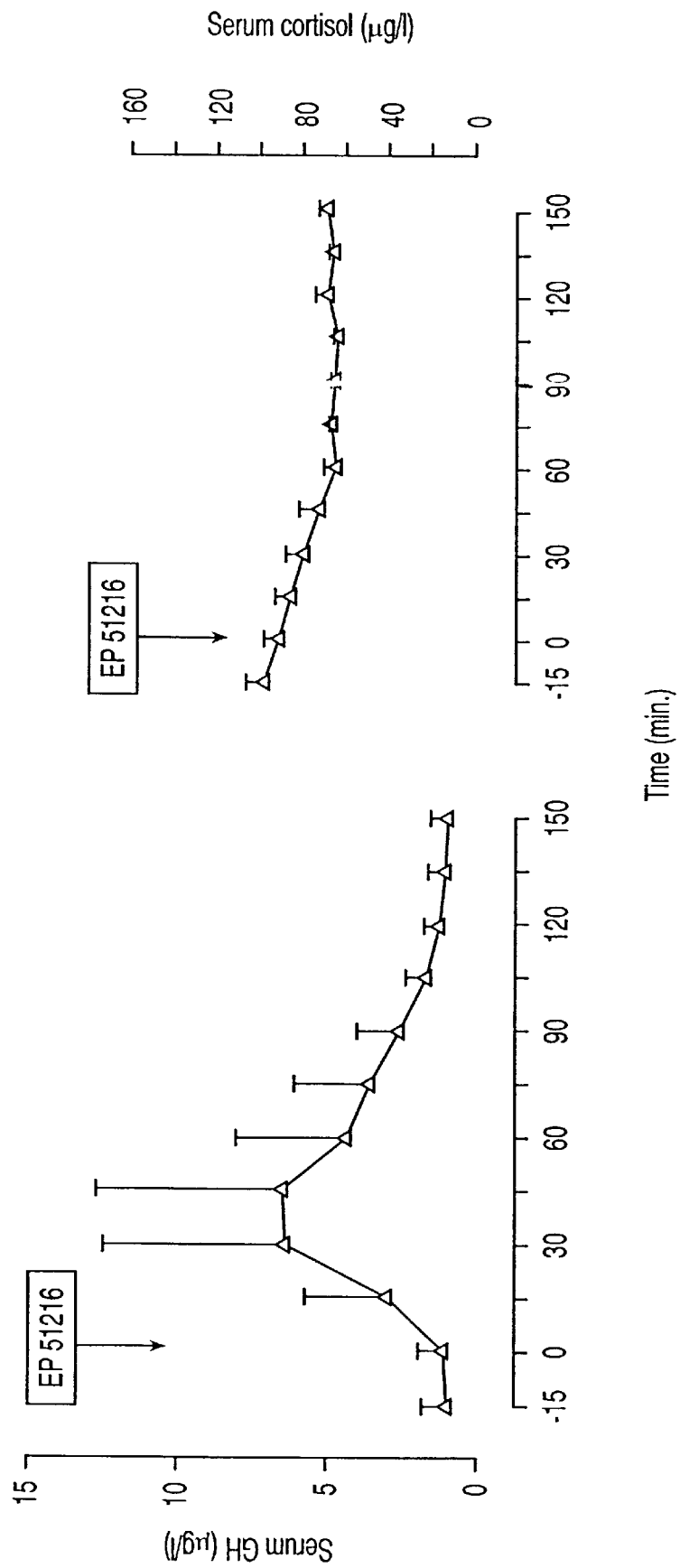
FIGS. 21A and 21B are graphs of the amount of growth hormone and cortisol released in humans after administration of the peptide of Example 17.

A capsule containing 20 mg of the peptide of Example 18 was orally administered to 5 healthy subjects (3 men and 2 women, ages 30 to 66) and serum growth hormone and cortisol levels were measured at various times after administration. Results are shown in FIGS. 21A and 21B. Surprisingly, growth hormone levels were increased without cortisol stimulation.

Examples 29–31

Figure 22:
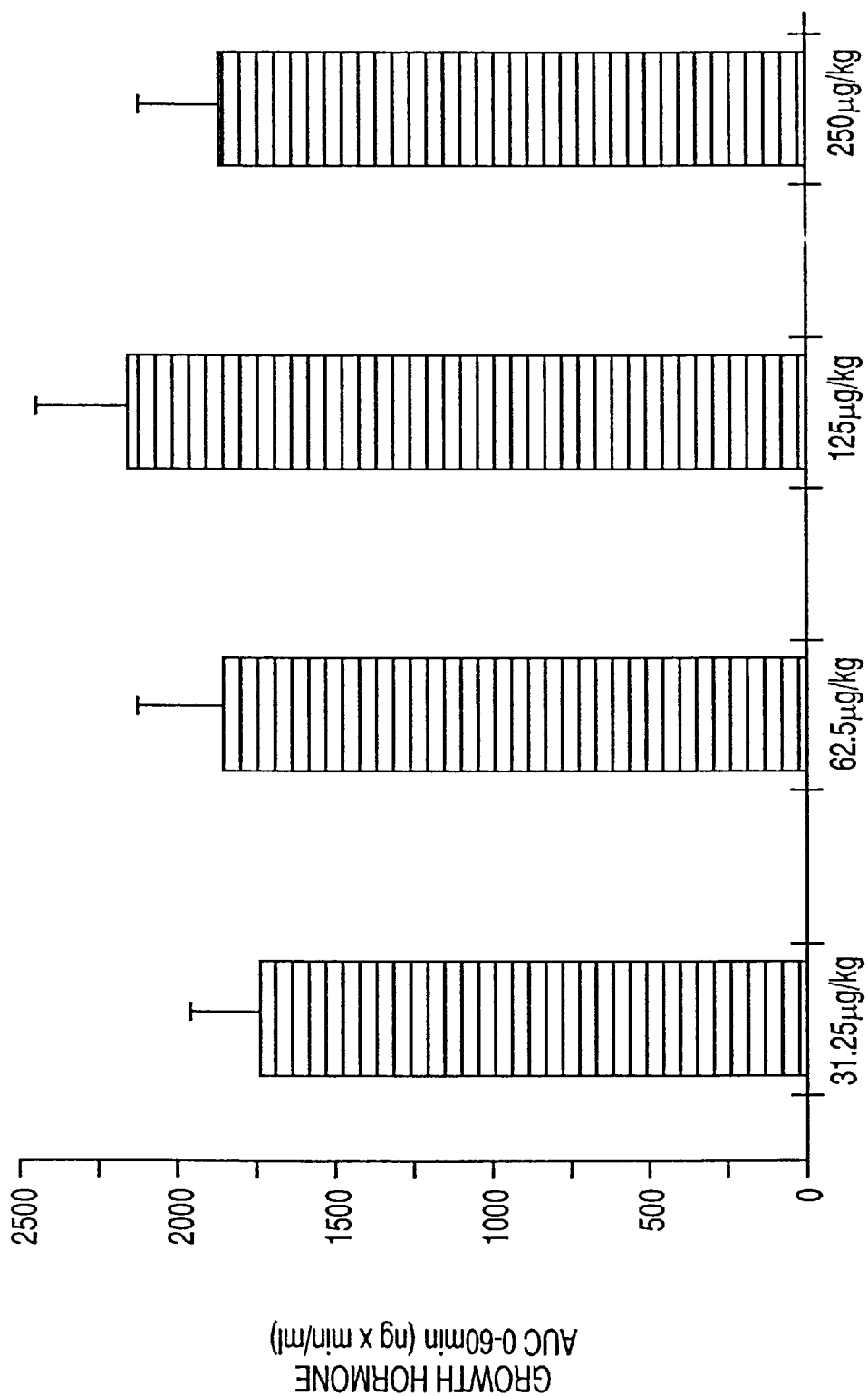
FIGS. 22–24 are graphs of the amount of growth hormone released in dogs after oral administration of various amounts of the peptide GAB-D-2-Mrp-D-βNal-Phe-Lys-NH$_2$ (FIG. 1) and Aib-D-2-Mrp-D-2-Mrp-NH$_2$ (FIGS. 2 and 3).
Figure 23:
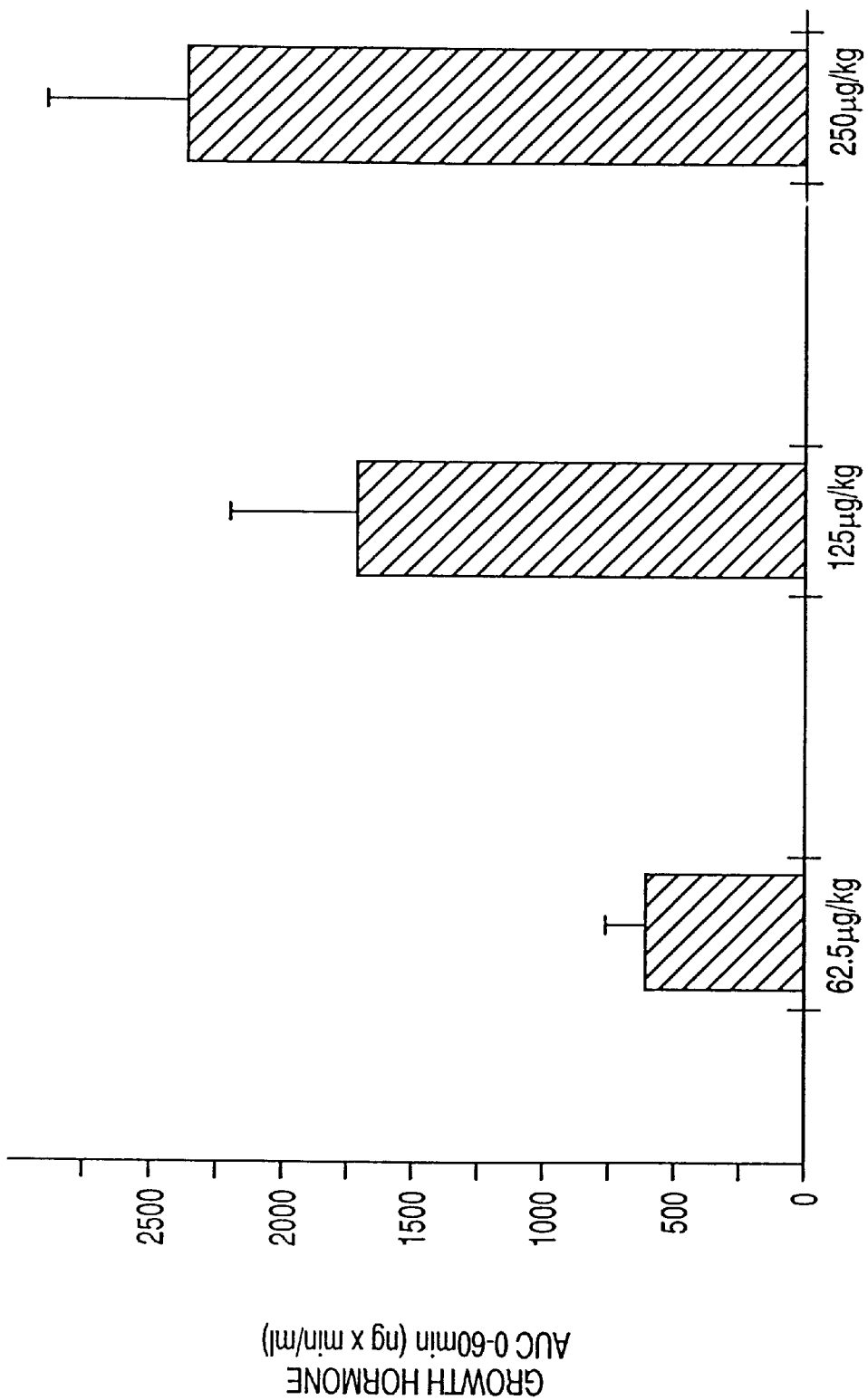
Figure 24:
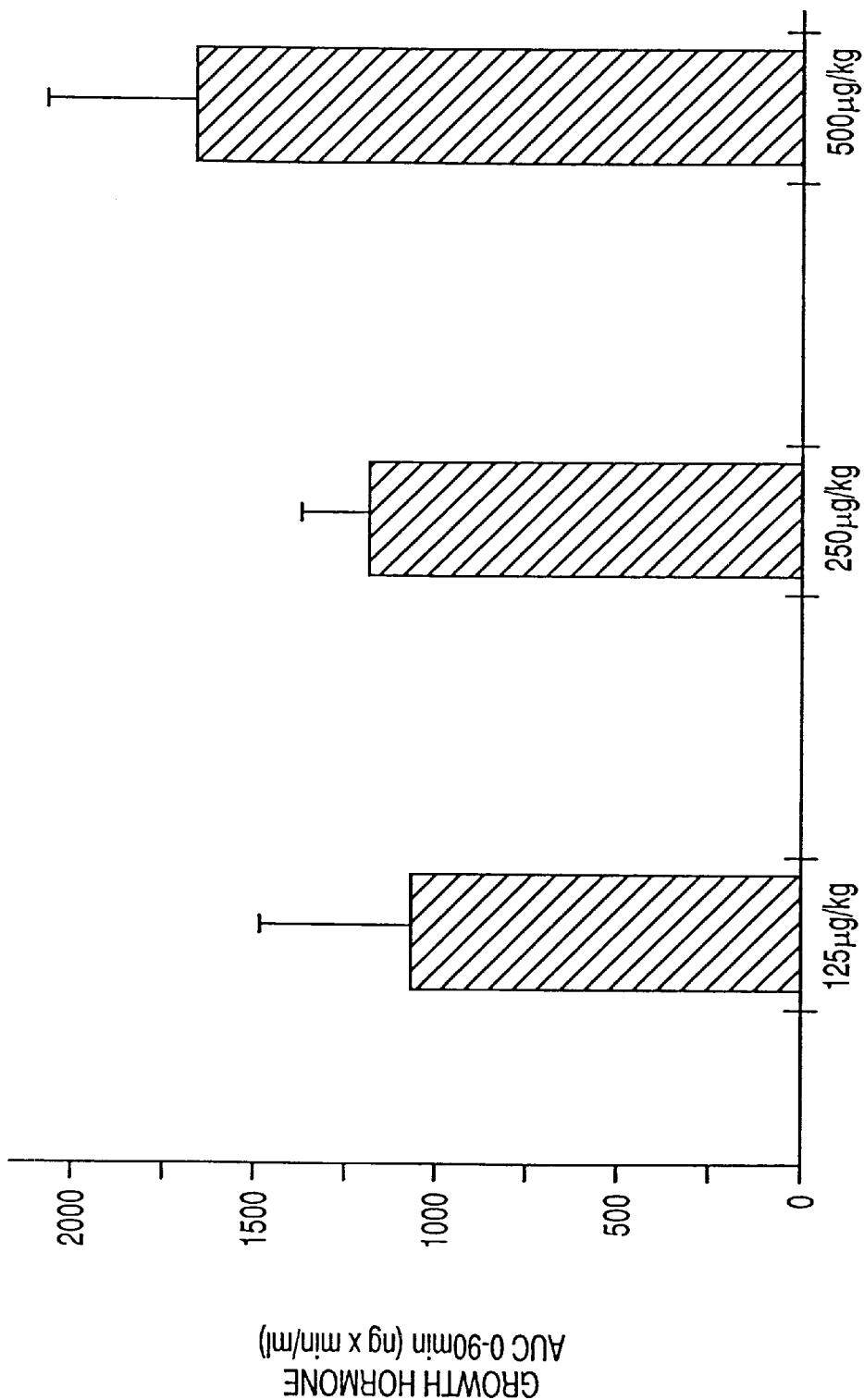

The peptides of Examples 18, 19 and 23 were selected for further study and were tested in vivo in adult dogs. The peptides were administered orally at a dosage of 1 mg/Kg. body weight. Results are shown in FIGS. 22–24.

Example 32–33

The peptides of Examples 19 and 23 were further studied for inhibition of $^{125}$I-Tyr-Ala-HEXARELIN binding to human tissue.

Tissue membranes (0.1 mg protein) obtained from the heart and hypothalamus of two different adult subjects were incubated in triplicate with a subsaturating concentration (34 pM, about 48,000 cpm, for heart tissue and 42 pM, about 60,000 cpm for hypothalamus tissue) of $^{125}$I-Tyr-Ala-HEXARELIN for 40 min at 0° C. in the absence and in the presence of increasing concentrations of the indicated unlabelled peptides. The value in parentheses represents the % of inhibition of $^{125}$I-Tyr-Ala-HEXARELIN specifically bound. Results are shown in Tables 7 and 8 below.

TABLE 7

| | Human heart tissue | | | | | |
|---|---|---|---|---|---|---|
| peptide concentration | HEXARELIN | | Example 19 | | Example 23 | |
| (nM) | subject 1 | subject 2 | subject 1 | subject 2 | subject 1 | subject 2 |
| 0 | 21.0 (0) | 23.9 (0) | 25.1 (0) | 24.6 (0) | 20.3 (0) | 24.0 (0) |
| 0.1 | 20.1 (4) | 22.8 (5) | 25.1 (0) | 24.5 (0) | 20.1 (1) | 23.8 (1) |
| 1 | 16.9 (20) | 17.3 (28) | 24.9 (1) | 24.5 (0) | 19.8 (3) | 23.5 (2) |
| 10 | 10.4 (51) | 10.5 (56) | 24.9 (1) | 24.0 (3) | 16.5 (19) | 19.2 (20) |
| 100 | 1.7 (92) | 2.4 (90) | 24.7 (2) | 24.1 (2) | 10.2 (50) | 11.2 (53) |
| 1000 | 0 (100) | 0 (100) | 24.4 (3) | 24.0 (3) | 4.0 (80) | 4.0 (83) |
| IC$_{50}$ value (nM) | 10.6 | 8.3 | inactive | inactive | 62.7 | 57 |
| mean IC$_{50}$ value (nM) | 9.5 | | — | | 59.8 | |
| comparative IC$_{50}$ value (HEXARELIN = 1) | 1 | | — | | 6 | |

TABLE 8

| peptide concentration | HEXARELIN | | Example 19 | | Example 23 | |
|---|---|---|---|---|---|---|
| (nM) | subject 1 | subject 2 | subject 1 | subject 2 | subject 1 | subject 2 |
| 0 | 11.2 (0) | 9.5 (0) | 11.0 (0) | 10.3 (0) | 10.2 (0) | 10.8 (0) |
| 0.1 | 10.7 (3) | 9.1 (4) | 9.8 (11) | 9.0 (13) | 9.1 (11) | 10.0 (7) |
| 1 | 9.6 (16) | 7.7 (19) | 8.3 (25) | 7.0 (32) | 8.8 (14) | 8.9 (18) |
| 10 | 5.2 (51) | 3.1 (67) | 3.9 (65) | 3.6 (75) | 3.8 (63) | 3.3 (69) |
| 100 | 1.2 (89) | 0.7 (93) | 1.0 (91) | 0.2 (98) | 2.1 (79) | 1.9 (82) |
| 1000 | 0 (100) | 0 (100) | 0 (100) | 0.1 (99) | 0.3 (97) | 0 (100) |
| $IC_{50}$ value (nM) | 8.9 | 5.0 | 6.0 | 3.6 | 6.2 | 4.5 |
| mean $IC_{50}$ value (nM) | 7.0 | | 4.8 | | 5.4 | |
| comparative $IC_{50}$ value (HEXARELIN = 1) | 1 | | 0.7 | | 0.8 | |

The specific binding of $^{125}$I-Tyr-Ala-HEXARELIN/0.1 mg membrane protein is expressed as a percent of total radioactivity added. Although HEXARELIN is useful, the results show that the peptide of Example 19 exhibits potent binding to hypothalamus tissue with no binding to heart tissue, while the peptide of Example 23 also exhibits strong binding to hypothalamus tissue with only moderate binding to heart tissue.

Example 34
Synthesis of GAB-D-Mrp-D-Trp-Phe-Lys-NH$_2$

The synthesis of the title peptide was carried out by solid-phase with 9-fluorenylmethyloxycarbonyl (Fmoc)-protected amino acids involving resin preparation and assembly in a reactor column according to one of several methods known to those skilled in the art, as exemplified in "Solid phase peptide synthesis" by E. Atherton and R. C. Sheppard, IRL press at Oxford University press, 1989. The protected amino acids are Fmoc-Lys(Fmoc)-Opfp (Opfp=pentafluorophenyl ester), Fmoc-Phe-Opfp, Fmoc-D-Trp-Opfp, Fmoc-D-2-Me-Trp-Opfp and Fmoc-GAB-Opfp (GAB=gamma-aminobutyryl). Alternatively, the use of Castro's reagents, benzotriazolyloxy-tris(dimethylamino) phosphonium (hexafluorophosphate) BOP and the pyridinium analog of BOP (PyBOP) (cfr. Le Nguyen and Castro (1988) in Peptide Chemistry 1987, p. 231–238; Protein Research Foundation Osaka; and Tetrahedron Letters 31, 205 (1990)) can be used advantageously as direct coupling reagents.

After cleavage and isolation, the title peptide was purified as its acetate salt. Purity (HPLC): 98%, MW (M+H$^+$)=764.3 (theoretical=763.9).

Example 35

The following peptides were prepared according to the procedures described in Example 34, isolated as their TFA (triflouroacetate) salts and whenever needed, purified as their acetate salts:

INIP-D-Mrp-D-Trp-Phe-Lys-NH$_2$, purity (HPLC)= 99.0%, MW (M+H$^+$=790.4; theoretical=790.0);

INIP-D-Mrp-D-β-Nal-Phe-Lys-NH$_2$, purity (HPLC)= 96.5%, MW (M+H$^+$=801.4; theoretical=801.0);

IMA-D-Mrp-D-Trp-Phe-Lys-NH$_2$, purity (HPLC)= 99.2%, MW (M+H$^+$=786.5; theoretical=786.8);

IMA-D-Mrp-D-β-Nal-Phe-Lys-NH$_2$, purity (HPLC)= 97.3%, MW (M+H$^+$=798.3; theoretical=797.9);

GAB-D-Mrp-D-β-Nal-Phe-Lys-NH$_2$;

GAB-D-Mrp-D-β-Nal-NH$_2$;

4-(aminomethyl)cyclohexanecarbonyl-D-Mrp-D-Trp-Phe-Lys-NH$_2$, purity (HPLC)=99.0%, MW (M+H$^+$= 818.5; theoretical=818.0);

4-(aminomethyl)cyclohexanecarbonyl-D-Mrp-D-β-Nal-Phe-Lys-NH$_2$, purity (HPLC)=96.9%, MW (M+H$^+$= 829.5; theoretical=829.1);

D-Ala-D-Mrp-Ala-Trp-D-Phe-Lys-NH$_2$, purity (HPLC)= 99.3%, MW (M+H$^+$=821.3; theoretical=821.9);

D-Thr-D-Mrp-Ala-Trp-D-Phe-Lys-NH$_2$, purity (HPLC)= 98.0%, MW (M+H$^+$=851.5; theoretical=852.0);

His-D-Mrp-Ala-Phe-D-Trp-Lys-NH$_2$, purity (HPLC)=22 98.6%, MW (M+H$^+$=887.4; theoretical=888.0);

Tyr-His-D-Mrp-Ala-Trp-D-Phe-Lys-NH$_2$, purity (HPLC)=96.8%, MW (M+H$^+$=1050.2; theoretical= 1050.2);

His-D-Mrp-Ala-Trp-NH$_2$, purity (HPLC)=99.8%, MW (M+H$^+$=612.3; theoretical=612.7);

D-Thr-D-Mrp-Ala-Trp-NH$_2$, purity (HPLC)=97.5%, MW (M+H$^+$=576.5; theoretical=576.6);

His-D-Mrp-Ala-Trp-D-Phe-Lys-Thr-NH$_2$;

His-D-Mrp-Ala-Trp-D-Phe-Lys-D-Thr-NH$_2$;

D-Thr-His-D-Mrp-Ala-Trp-D-Phe-Lys-NH$_2$; and imidazolylacetyl-D-Mrp-Ala-Trp-D-Phe-Lys-NH$_2$, wherein Mrp is 2-methyltryptophan, and INIP, IMA and GAB are as defined above.

Example 36
Synthesis of GAB-D-Mrp-D-β-Nal-OC$_2$H$_5$.

The peptide GAB-D-Mrp-D-β-Nal-OC$_2$H$_5$, bearing an ethyl ester in the C-terminal position, was synthesized via solution-phase synthesis according to conventional methods such as those described in of Bodansky et al., Peptide Synthesis, 2nd edition, John Wiley & Sons, New York, N. Y. 1976 and Jones, The Chemical Synthesis of Peptides (Clarendon Press, Oxford, 1994), wherein the starting material used in the synthesis of the title compound was D-β-naphthylalanine ethyl ester.

Example 37
Biological Activity

In vivo activity of these compounds was determined in ten day-rats, which were subcutaneously injected (s.c.) with a dose of 300 μg/kg or with different doses in dose-response studies, according to the procedure as described in Deghenghi et. al, Life Sciences 54, 1321 (1994). The results are shown in Table 9, below. The released GH was measured 15 minutes following compound administration.

TABLE 9

| Peptide | Dose μg/kg s.c. | GH control (ng/ml) | GH released (ng/ml) |
| --- | --- | --- | --- |
| His-D-Mrp—Ala—Trp-D-Phe—Lys—Thr—NH$_2$ | 300 | 31 ± 8 | 176 ± 20 |
| His-D-Mrp—Ala—Trp-D-Phe—Lys—NH$_2$ | 300 | 14.7 ± 1.9 | 104.2 ± 13.1 |
| His-D-Mrp—Ala—Trp-D-Phe—Lys-D-Thr—NH$_2$ | 300 | 31 ± 8 | 169 ± 27 |
| D-Thr-D-Mrp—Ma—Trp-D-Phe—Lys—NH$_2$ | 300 | 31 ± 8 | 266 ± 20 |
| D-Thr—His-D-Mrp—Ala—Trp-D-Phe—Lys—NH$_2$ | 300 | 31 ± 8 | 86 ± 19 |
| D-Ala-D-Mrp—Ala—Trp-D-Phe—Lys—NH$_2$ | 40 | 34 ± 1 | 200 ± 20 |
| D-Ala-D-Mrp—Ala—Trp-D-Phe—Lys—NH$_2$ | 320 | 34 ± 1 | 251 ± 32 |
| His-D-Mrp—Ala—Trp—NH$_2$ | 5000 | 69 ± 14 | 124 ± 37 |
| imidazolylacetyl-D-Mrp—Ala—Trp-D-Phe—Lys—NH$_2$ | 300 | 20 ± 3 | 159 ± 27 |
| imidazolylacetyl-D-Mrp-D-Trp—Phe—Lys—NH$_2$ | 300 | 14.7 ± 1.9 | 60.3 ± 8.1 |
| imidazolylactyl-D-Mrp-D-β-Nal—Phe—Lys—NH$_2$ | 300 | 14.7 ± 1.9 | 56.0 ± 12.4 |
| INIP-D-Mrp-D-Trp—Phe—Lys—NH$_2$ | 300 | 15 | 155 |
| INIP-D-Mrp-D-Trp—Phe—Lys—NH$_2$ | 300 | 14.7 ± 1.9 | 119.5 ± 18.6 |
| INIP-D-Mrp-D-β-Nal—Phe—Lys—NH$_2$ | 300 | 15 | 150 |
| INIP-D-Mrp-D-β-Nal—Phe—Lys—NH$_2$ | 300 | 14.7 ± 1.9 | 125.9 ± 13.0 |
| 4-(aminomethyl)cyclohexanecarbonyl-D-Mrp-D-Trp—Phe—Lys—NH$_2$ | 300 | 14.7 ± 1.9 | 111.8 ± 24.6 |
| GAB-D-Mrp-D-Trp—Phe—Lys—NH$_2$ | 300 | 10 | 110 |
| GAB-D-Mrp-D-Trp—Phe—Lys—NH$_2$ | 300 | 14.7 ± 1.9 | 172.8 ± 15.8 |
| GAB-D-Mrp-D-β-Nal—Phe—Lys—NH$_2$ | 300 | 14.7 ± 1.9 | 198.0 ± 13.2 |
| (GHRP-2) - reference | 300 | 10 | 98.6 |
| (GHRP-2) - reference | 300 | 14.7 ± 1.9 | 154.4 ± 18.5 |

The GHRP-2 (reference standard) has the structure D-Ala-D-β-Nal-Ala-Trp-D-Phe-Lys-NH$_2$ (Chen and Clarke, J. Neuroend. 7, 179 (1995).

In vitro measurements of adenylcyclase activity were determined in anterior pituitary gland cells from rats weighing 150 g and showed a 30% increase compared with the baseline with EC$_{50}$=0.23 nM for the peptide D-Ala-D-Mrp-Ala-Trp-D-Phe-Lys-NH$_2$, whereas GHRP-6 (His-D-Trp-Ala-Trp-D-Phe-Lys-NH$_2$) resulted inactive.

From the foregoing examples, it is evident that the incorporation of a D-2-methyl-tryptophan residUe in the peptides of the invention result in increased activity ranging from 30–40 ng/ml to over 200 ng/ml. Also, this increased activity is tissue selective for certain peptides. For these reasons, the peptides of this invention have greater pharmacological utility than the corresponding peptides that do not contain D-2-Mrp.

While it is apparent that the invention herein disclosed is well calculated to fulfill the objects above stated, it will be appreciated that numerous embodiments and modification may be devised by those skilled in the art, and it is intended that the appended claims cover all such modification and embodiments as fall within the true spirit and scope of the present invention.

What is claimed is:

1. A method for enhancing the growth hormone release which comprises formulating a composition comprising a peptide having an amino acid sequence which includes at least one D-2-alkylTryptophan that has a lower alkyl group substituted at the number 2 position, and administering a therapeutically effective amount of the composition to an animal to obtain enhanced growth hormone release compared to the release evoked by peptides that have conventional Tryptophan in place of the D-2-alkylTryptophan.

2. The method according to claim 1, wherein the animal is a human.

3. The method according to claim 1, wherein the peptide is administered intravenously in an amount of about 0.1 μg to about 10 μg of total peptide per kg of body weight.

4. The method of claim 1 wherein the peptide sequence contains between 2 and 10 amino acids, wherein at least one amino acid is the D-2-alkylTryptophan.

5. The method of claim 4 wherein the peptide sequence contains at least two amino acids which are D-2-alkylTryptophan.

6. The method of claim 5, wherein the two D-2-alkylTryptophans are in adjacent positions in the peptide sequence.

7. The method of claim 1, wherein the lower alkyl group is methyl, ethyl, propyl or isopropyl.

8. The method of claim 1, wherein the lower alkyl group is a methyl group.

9. The method of claim 1, wherein the peptide has one of the following formulae:

A—D—X—Z—B              (I)

E—D—Mrp—(Ala)$_n$—F—G              (II)

J—D—X—Mrp—NH$_2$              (III)

wherein

A is hydrogen, 2-aminoisobutyryl, or 4-aminobutyryl;

D stands for the dextro isomer,

X is a 2-alkyltryptophan of formula (IV):

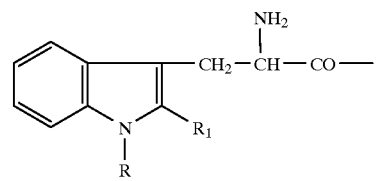

wherein R is hydrogen, CHO, SO$_2$CH$_3$, mesitylene-2-sulfonyl, PO$_3$(CH$_3$)$_2$, PO$_3$H$_2$, wherein R$_1$ is a C$_1$–C$_3$ alkyl group (e.g., methyl, ethyl, propyl or isopropyl), or X is a residue of protected serine, Ser (Y), wherein Y can be benzyl, p-chlorobenzyl, 4-methoxybenzyl, 2,4,6-trimethoxybenzyl, or t-butyl, Z is D-Mrp, D-βNal or Mrp;

Mrp is 2-alkyl-Tryptophan;

B is NR$_2$R$_3$, wherein R$_2$ and R$_3$, which can be the same or different, are hydrogen, a C$_1$–C$_3$ alkyl group, an OR$_4$ group, wherein $R_4$ is hydrogen, a $C_1$–$C_3$ alkyl, or a C-Lys-NH$_2$ group, wherein C is Phe, Mrp or D-Mrp;

E is any natural L-amino acid or its D-isomer, imidazolylacetyl, isonipecotinyl, 4-aminobutyryl, 4-(aminomethyl)cyclohexanecarbonyl, Glu-Tyr-Ala-His, Tyr-Ala-His, Tyr-His, D-Thr-His, D-Ala, D-Thr, Tyr and Gly;

n is 0 or 1;

F is selected from the group consisting of Trp, D-Trp, Phe and D-β-Nal;

G is selected from the group consisting of NH$_2$, D-Phe-Lys-NH$_2$, Phe-Lys-NH$_2$, D-Trp-Lys-NH$_2$, D-Phe-Lys-Thr-NH$_2$, D-Phe-Lys-D-Thr-NH$_2$ and an O—C$_1$–C$_3$ alkyl group, with the proviso that E is not His when F is L-Trp or D-Trp and when G is D-Phe-Lys-NH$_2$; and J is hydrogen, GAB or D-Mrp;

or os a pharmaceutically acceptable addition salt thereof.

10. The method of claim 1, wherein the peptide is

GAB-D-Mrp-D-Mrp-Phe-Lys-NH$_2$;
GAB-D-Mrp-D-Mrp-Mrp-Lys-NH$_2$;
Aib-D-Mrp-D-Mrp-NH$_2$;
Aib-D-Mrp-Mrp-NH$_2$;
Aib-D-Ser(Bzl)-D-Mrp-NH$_2$;
GAB-D-Mrp-D-βNal-Phe-Lys-NH$_2$;
GAB-D-Mrp-D-Mrp-D-Mrp-Lys-NH$_2$;
D-Mrp-D-Mrp-Mrp-NH$_2$;
GAB-D-Mrp-Mrp-NH$_2$;
D-Mrp-Mrp-NH$_2$
INIP-D-Mrp-D-Trp-Phe-Lys-NH$_2$;
INIP-D-Mrp-D-β-Nal-Phe-Lys-NH$_2$;
IMA-D-Mrp-D-Trp-Phe-Lys-NH$_2$;
IMA-D-Mrp-D-β-Nal-Phe-Lys-NH$_2$;
GAB-D-Mrp-D-Trp-Phe-Lys-NH$_2$;
GAB-D-Mrp-D-β-Nal-Phe-Lys-NH$_2$;
GAB-D-Mrp-D-β-Nal-NH$_2$;
imidazolylacetyl-D-Mrp-Ala-Trp-D-Phe-Lys-NH$_2$;
imidazolylacetyl-D-Mrp-D-Trp-Phe-Lys-NH$_2$;
imidazolylacetyl-D-Mrp-D-β-Nal-Phe-Lys-NH$_2$;
4-(aminomethyl)cyclohexanecarbonyl-D-Mrp-D-Trp-Phe-Lys-NH$_2$;
4-(aminomethyl)cyclohexanecarbonyl-D-Mrp-D-β-Nal-Phe-Lys-NH$_2$;
D-Ala-D-Mrp-Ala-Trp-D-Phe-Lys-NH$_2$;
D-Thr-D-Mrp-Ala-Trp-D-Phe-Lys-NH$_2$;
His-D-Mrp-Ala-Phe-D-Trp-Lys-NH$_2$;
His-D-Mrp-Ala-Trp-D-Phe-Lys-Thr-NH$_2$;
His-D-Mrp-Ala-Trp-D-Phe-Lys-D-Thr-NH$_2$;
Tyr-His-D-Mrp-Ala-Trp-D-Phe-LysNH$_2$;
His-D-Mrp-Ala-TrpNH$_2$;
D-Thr-His-D-Mrp-Ala-Trp-D-Phe-Lys-NH$_2$;
D-Thr-D-Mrp-Ala-TrpNH$_2$; or
GAB-D-Mrp-D-β-Nal-OC$_2$H$_5$ and pharmaceutically acceptable salts thereof, wherein Mrp is 2-methyltryptophan.

* * * * *